(12) United States Patent
Tondra

(10) Patent No.: US 7,446,524 B2
(45) Date of Patent: Nov. 4, 2008

(54) METHOD FOR DETECTING MAGNETIC PARTICLES IN A FLUID USING THIN-FILM MAGNETIC FIELD SENSOR

(75) Inventor: Mark C. Tondra, Minneapolis, MN (US)

(73) Assignee: NVE Corporation, Eden Prairie, MN (US)

( * ) Notice: Subject to any disclaimer, the term of this patent is extended or adjusted under 35 U.S.C. 154(b) by 0 days.

(21) Appl. No.: 11/809,254

(22) Filed: May 31, 2007

(65) Prior Publication Data

US 2007/0236212 A1    Oct. 11, 2007

Related U.S. Application Data

(60) Division of application No. 11/048,217, filed on Feb. 1, 2005, now Pat. No. 7,235,969, which is a continuation of application No. 09/799,429, filed on Mar. 5, 2001, now Pat. No. 6,875,621, which is a continuation-in-part of application No. 09/687,791, filed on Oct. 13, 2000, now Pat. No. 6,743,639.

(60) Provisional application No. 60/159,185, filed on Oct. 13, 1999.

(51) Int. Cl.
  *G01N 27/74* (2006.01)
  *G01R 33/12* (2006.01)
(52) U.S. Cl. .................. 324/204; 324/252; 324/249
(58) Field of Classification Search ............... 324/204, 324/239, 244–252
  See application file for complete search history.

(56) References Cited

U.S. PATENT DOCUMENTS

| | | | | |
|---|---|---|---|---|
| 114,591 A | * | 5/1871 | Notman | .......................... 56/384 |
| 165,633 A | * | 7/1875 | Walther | ........................ 164/247 |
| 4,679,107 A | * | 7/1987 | Imakoshi et al. | ............... 360/66 |
| 5,186,827 A | * | 2/1993 | Liberti et al. | ................. 210/222 |
| 5,466,574 A | * | 11/1995 | Liberti et al. | ................... 435/5 |
| 5,498,298 A | * | 3/1996 | Wecker et al. | ............... 148/105 |
| 5,569,544 A | * | 10/1996 | Daughton | ................ 428/811.3 |
| 5,650,887 A | * | 7/1997 | Dovek et al. | ................... 360/75 |
| 5,656,429 A | * | 8/1997 | Adelman | ......................... 435/6 |
| 5,660,990 A | * | 8/1997 | Rao et al. | ........................ 435/6 |
| 5,668,473 A | * | 9/1997 | Van Den Berg | ............. 324/252 |
| 5,686,838 A | * | 11/1997 | van den Berg | ............... 324/252 |
| 5,691,936 A | * | 11/1997 | Sakakima et al. | ............ 365/158 |
| 5,750,270 A | * | 5/1998 | Tang et al. | ................... 428/611 |
| 5,831,426 A | * | 11/1998 | Black et al. | .................. 324/127 |
| 5,895,727 A | * | 4/1999 | Hasegawa | ................ 428/811.4 |

(Continued)

*Primary Examiner*—Jay M Patidar
(74) *Attorney, Agent, or Firm*—Kinney & Lange, P.A.

(57) ABSTRACT

A ferromagnetic thin-film based magnetic field detection system used for detecting the presence of selected molecular species. A magnetic field sensor supported on a substrate has a binding molecule layer positioned on a side thereof capable of selectively binding to the selected molecular species held on a magnetic particle. The magnetic field sensor can be substantially covered by an electrical insulating layer having a recess therein adjacent to the sensor in which the binding molecule layer is provided. A thin-film channel structure to the sensor is supported on the substrate that can be accompanied by a reservoir structure, and an electrical interconnection conductor is supported on the substrate at least in part between the sensor and the substrate, and is electrically connected to the sensor. The magnetic field sensor can be provided in a bridge circuit, and can be formed by a number of interconnected individual sensors.

2 Claims, 25 Drawing Sheets

U.S. PATENT DOCUMENTS

| | | | |
|---|---|---|---|
| 5,949,707 A * | 9/1999 | Pohm et al. | 365/158 |
| 5,981,297 A * | 11/1999 | Baselt | 436/514 |
| 5,985,153 A * | 11/1999 | Dolan et al. | 210/695 |
| RE36,517 E * | 1/2000 | Araki et al. | 427/132 |
| 6,046,585 A * | 4/2000 | Simmonds | 324/239 |
| 6,057,167 A * | 5/2000 | Shieh et al. | 436/526 |
| 6,074,743 A * | 6/2000 | Araki et al. | 428/332 |
| 6,074,767 A * | 6/2000 | Lin | 428/811.2 |
| 6,083,632 A * | 7/2000 | Fujikata et al. | 428/611 |
| 6,090,480 A * | 7/2000 | Hayashi | 428/811.2 |
| 6,114,056 A * | 9/2000 | Inomata et al. | 428/811.1 |
| 6,124,711 A * | 9/2000 | Tanaka et al. | 324/252 |
| 6,462,541 B1 * | 10/2002 | Wang et al. | 324/252 |
| 6,736,978 B1 * | 5/2004 | Porter et al. | 210/695 |
| 2002/0119470 A1 * | 8/2002 | Nerenberg et al. | 435/6 |

* cited by examiner

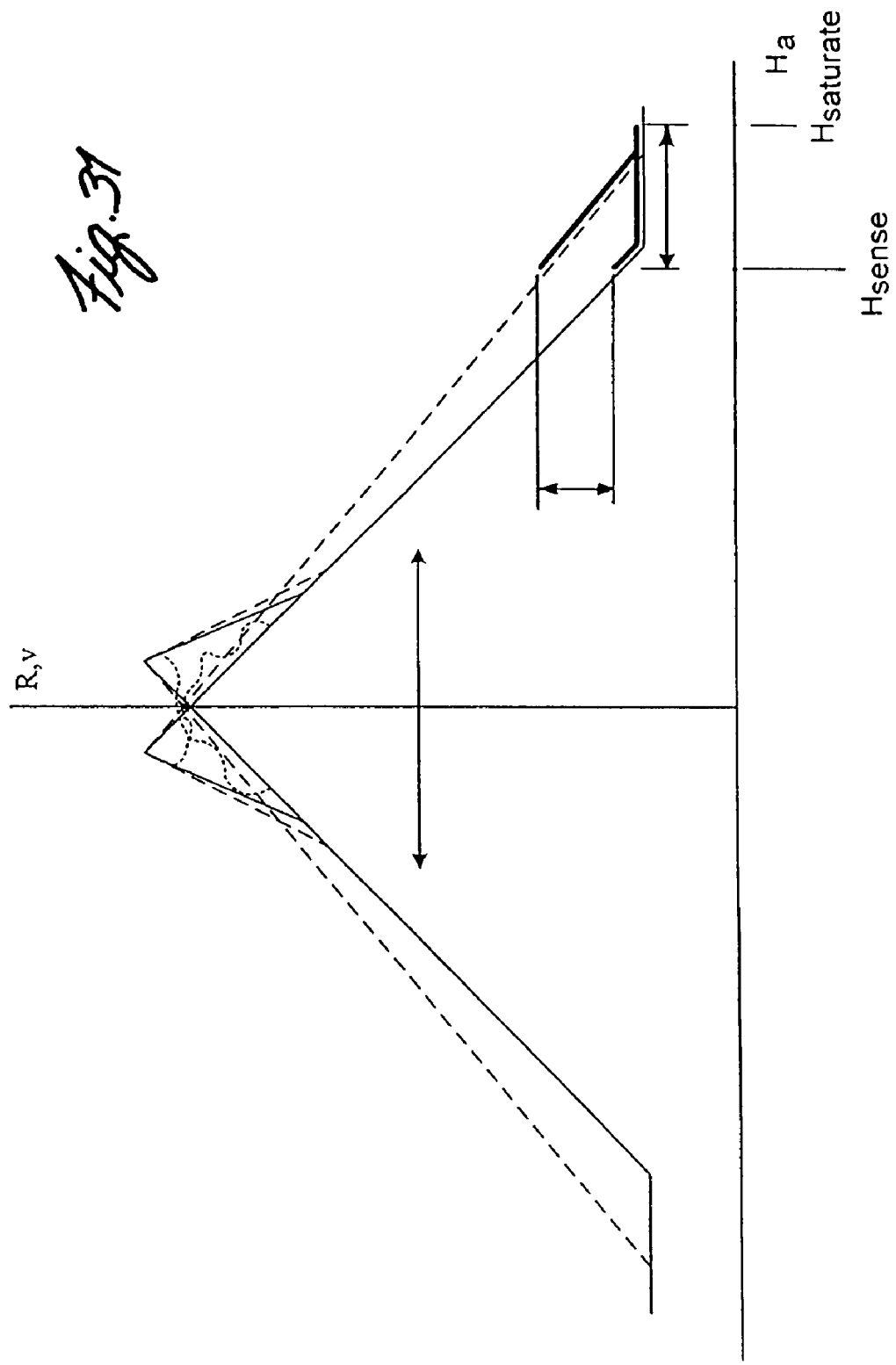

METHOD FOR DETECTING MAGNETIC PARTICLES IN A FLUID USING THIN-FILM MAGNETIC FIELD SENSOR

CROSS-REFERENCE TO RELATED APPLICATIONS

This application is a divisional application of application Ser. No. 11/048,217 filed Feb. 1, 2005 for "Magnetizable Bead Detector" by Mark C. Tondra, which is a continuation application of application Ser. No. 09/799,429 filed Mar. 5, 2001, for "Magnetizable Bead Detector" by Mark C. Tondra, which is a continuation-in-part application of application Ser. No. 09/687,791, filed Oct. 13, 2000 for "Magnetizable Bead Detector by Mark C. Tondra and John M. Anderson, which claims priority from Provisional Application No. 60/159,185, filed Oct. 13, 1999 for "Magnetizable Bead Assay".

BACKGROUND

The present invention relates to the detection of magnetizable beads and, more particularly, to detection of magnetizable beads in connection with biological and chemical assays.

Among the biomolecular detection methods used to detect selected molecules in the presence of other kinds of molecules mixed therewith are binding assays which are based on use of certain binding molecules to capture through specific chemical bondings the molecules selected for detection. Such specific bondings include polynucleic acid bondings or hybridizations involving DNA and RNA, antibody to antigen bondings, and various ligand to various receptor bondings. The detection of the selected molecules may be of primary interest in its own right, but may instead be of primary interest in indicating the presence of some other analyte molecule, species or organism.

Our arrangement for implementing such a detection scheme is to provide a sensor in which the binding molecules are relatively strongly attached to a solid substrate. An assay is begun by applying a sample solution containing various kinds of molecules possibly including the molecules selected for detection to the sensor along with label molecules attached to label beads (or particles) also present in the sample solution or in a supplemental solution concurrently also capture the selected molecules or the label molecules attached to label beads, or both, and thereafter hold them at the corresponding capture sites, i.e. the sites of the binding molecules undergoing such a bonding.

Label molecules on label beads are needed so that the occurrence of a recognition event leads to some measurable signal to indicate that a selected molecule was found present. One kind of label bead for doing this is a paramagnetic material bead having magnetizations that depend on externally applied magnetic fields. Application of such an externally applied field forcefully draws away any unbound label beads leaving the bound label beads at the capture sites while also magnetizing those bound label beads. Magnetic field detectors at the capture sites must sense the anomalies introduced into the externally applied field by the presence of bound label beads to produce the desired signals indicating the number of, and possibly the location of, such bound label beads. From this information the number of selected molecules, and kinds thereof, in the sample solution can be determined.

Such label beads can range in magnetic material composition from pure ferromagnetic material (e.g. permalloy) to small percentages of paramagnetic material encapsulated in plastic or ceramic spheres. As indicated above, such label beads are typically coated with a chemical or biological species that selectively binds to the selected molecules in an analyte of interest including DNA, RNA, viruses, bacteria, microorganisms, proteins, etc. to define the assay function, or the kind of recognition events, to be associated with that bead.

However, the label beads must typically be very small, that is, on the order of a few to tens of nanometers (nm) up to maybe a hundred or so or even up to a few microns in some instances. As a result the anomalies in an externally applied field will be very small. Thus, there is a desire for suitable magnetic field detectors for use with such beads.

SUMMARY

The present invention provides a ferromagnetic thin-film based magnetic field detection system used for detecting the presence of selected molecular species. The system has a magnetic field sensor supported on a substrate with a binding molecule layer positioned on a side thereof capable of selectively binding to the selected molecular species. The magnetic field sensor is substantially covered by an electrical insulating layer which in some embodiments has a recess therein adjacent to the sensor in which the bind molecule layer is provided. An electrical interconnection conductor is supported on the substrate at least in part between the sensor and the substrate in some embodiments, and is electrically connected to the sensor. The magnetic field sensor can be provided in a bridge circuit, and can be formed by a number of interconnected individual sensors located adjacent to the binding molecule layer. A thin-film channel structure on the substrate to the sensor is provided for the system which can be accompanied by a reservoir structure.

BRIEF DESCRIPTION OF THE DRAWINGS

FIG. 31 shows a characteristic diagram of a detector device.

DETAILED DESCRIPTION

The need for a very sensitive magnetic field detector follows from the smallness of the label beads and that the field anomalies caused thereby in an otherwise more or less uniform externally applied magnetic field are very localized in roughly decaying as $1/r^3$, where r is the magnitude of the distance from the center of a bead. Because of this highly localized field, only the sensor structure within about one bead diameter sees an appreciable magnetic field effect. Yet, of course, the largest signal possible from a given label bead is desired without suffering nonlinear effects due to bead to bead interactions. The applied field disruption from a label bead that is detected by a sensor is proportional to the magnetization of that bead.

Commercially available paramagnetic beads have either a small, or are entirely devoid of, remnant magnetization (i.e., the magnetization remaining in the bead after an externally applied magnetic field is removed). Consequently, a magnetic detector arrangement requires an additional externally applied magnetic field to magnetize the beads in any assay. The detector design must be such that detection can take place in an externally applied magnetic field optimal for detection, but not have the detection sensor response saturated, and not mask the field anomaly provided by the presence of a label bead.

Figure 1:
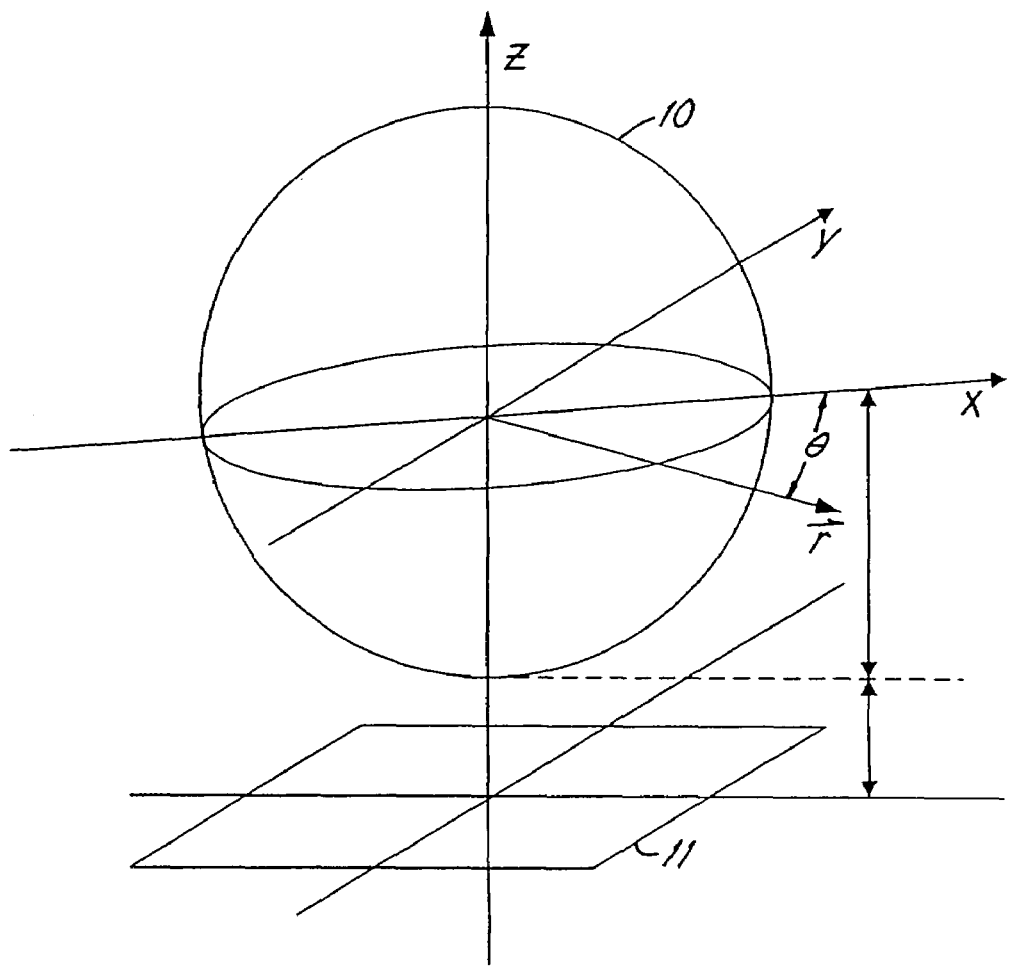
FIG. 1 shows a coordinate definition schematic diagram.

In these circumstances, the nature of a label bead anomaly induced in an externally applied field can be approximated by considering a sphere, 10, of paramagnetic material present in a uniform, externally applied, magnetic field of magnitude $H_{app}$ directed from left to right along the x axis in FIG. 1 parallel to the surface supporting the bead and a magnetic field detector, 11, shown diagrammatically therebelow. (Detector 11 is assumed here to not significantly affect the magnetic fields present.) Using mks units, magnetic induction B (Webers/meter$^2$), magnetic field strength H, and material magnetization M are related as (bold type denoting vector quantities)

$$B=\mu_0(H+M),$$

and $$M=\chi_m H_{app},$$

where $\chi_m$ is the dimensionless magnetic susceptibility. The entities "magnetizable beads" is defined in terms of the susceptibility $\chi_m$. While $\chi_m$ can be measured for any material, only some materials have values substantially different from zero ($\chi_m$ of empty space is zero). A paramagnetic material has a single-valued $\chi_m$ just greater than zero, typically ~0.001, while a ferromagnetic material has a multivalued $\chi_m$ (due to hysteresis) that is much larger than zero (typically ~1). As will become clear in the following analysis, larger values for $\chi_m$ lead to larger signals at the detector. However, ferromagnetic particles have a tendency to agglomerate because of magnetic attraction to one another (which potentially ruins an assay) and the multivalued nature of $\chi_m$ for such material leads to difficulties in quantification of surface coverage. Consequently, the typical assay employs a paramagnetic material magnetizable bead with as large a $\chi_m$ as possible without causing agglomeration. A spherical bead of a paramagnetic or ferromagnetic material will be uniformly magnetized in a uniform externally applied magnetic field. The external field contribution from the magnetizing of bead 10 will have a dipole distribution based on an effective dipole moment p of $$p=M(4\pi/3)a^3$$

where a is the bead radius, and M (Webers/meter) is the bead magnetization as indicated above.

If the origin is taken at the center of bead 10 in a spherical coordinate system as shown in FIG. 1, this dipole field will have no azimuthal angular dependence and can be represented by just two vector components. These two components of the dipole field at distance r from the center of bead 10 are $$H_r = \chi_m H_{app}(8\pi/3)\_(a^3/r^3)\cos(\theta),$$

and $$H_\theta = \chi_m H_{app}(4\pi/3)\_(a^3/r^3)\sin(\theta)$$

where θ is the angle between r and M (which follows the direction of the externally applied field $H_{app}$ along the x axis). The $1/r^3$ dependence of these field components can clearly be seen.

Figure 2:
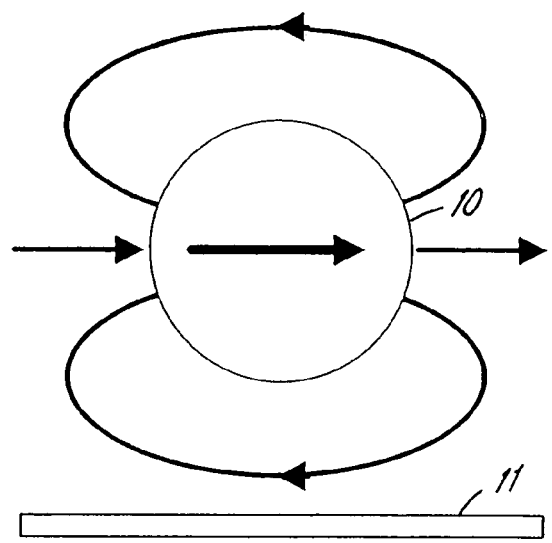
FIG. 2 shows a magnetizable sphere based magnetic response field schematic over a structure.

The magnetic field contribution alone from bead 10 positioned over magnetic field detector structure 11 in a uniform applied field directed from left to right is roughly depicted in FIG. 2. Similar structures and features in subsequent figures have the same numerical designations as were used in the preceding figures. The total field outside this bead in such an externally applied field will be the sum of the uniform applied field directed from left to right and the field contribution from bead 10 which contribution thus results in an anomaly in the otherwise uniform field present. Note that the field contribution directly under bead 10 in FIG. 2 (field contribution at θ=π/2 in FIG. 1) due to its magnetization will directly oppose the externally applied field thereby decreasing the total field value in this vicinity. The total field $H_{total}$ at magnetic field detector structure 11 directly under bead 10 is, as stated, the sum of the externally applied field $H_{app}$ and the field contribution from bead 10 due to its magnetization, $H_B$, or $$H_{total}=H_{app}+H_B=H_{app}+H_\theta$$

since the radial component does not contribute at θ=π/2.

Substituting for $H_\theta$ from above yields $$H_{total} = H_{app}\left\{1-\left[\chi_m\left(\frac{4\pi}{3}\right)\left(\frac{a^3}{r^3}\right)\sin(\theta)\right]\right\}$$

$$= H_{app}\left\{1-\left[\chi_m\left(\frac{4\pi}{3}\right)\left(\frac{a^3}{r^3}\right)\right]\right\}.$$

Figure 3:
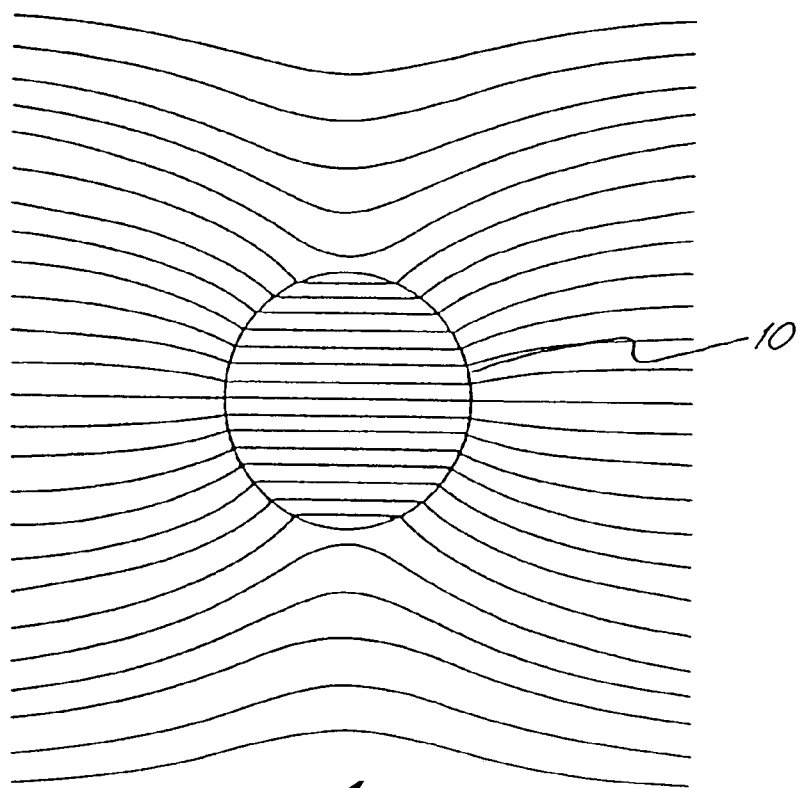
FIG. 3 shows a direction lines schematic for a magnetizable sphere in a uniform externally applied field.

A plot of the direction lines of this total field about bead 10 (independent of the azimuthal angle) is shown in FIG. 3 (which assumes that flux arising because of permeable material in a detector structure therebelow is negligible or is confined in a closed flux path therein). If the distance from the bottom surface of bead 10 to the upper surface of magnetic field detector structure 11 is equal to the radius of bead 10 (i.e., at the point having coordinates r=2a, θ=π/2) then $$H_{total}=H_{app}[1-\chi_m(\pi/6)].$$

A practical superparamagnetic bead (having a magnetization in a magnetic field much greater than ordinary paramagnetic material) has a value for $\chi_m$ around 0.05, so the total field at magnetic field detector structure 11 would be on the order of $$H_{total}=H_{app}[1-0.05(\pi/6)]\approx(0.97)H_{app}.$$

Figure 4:
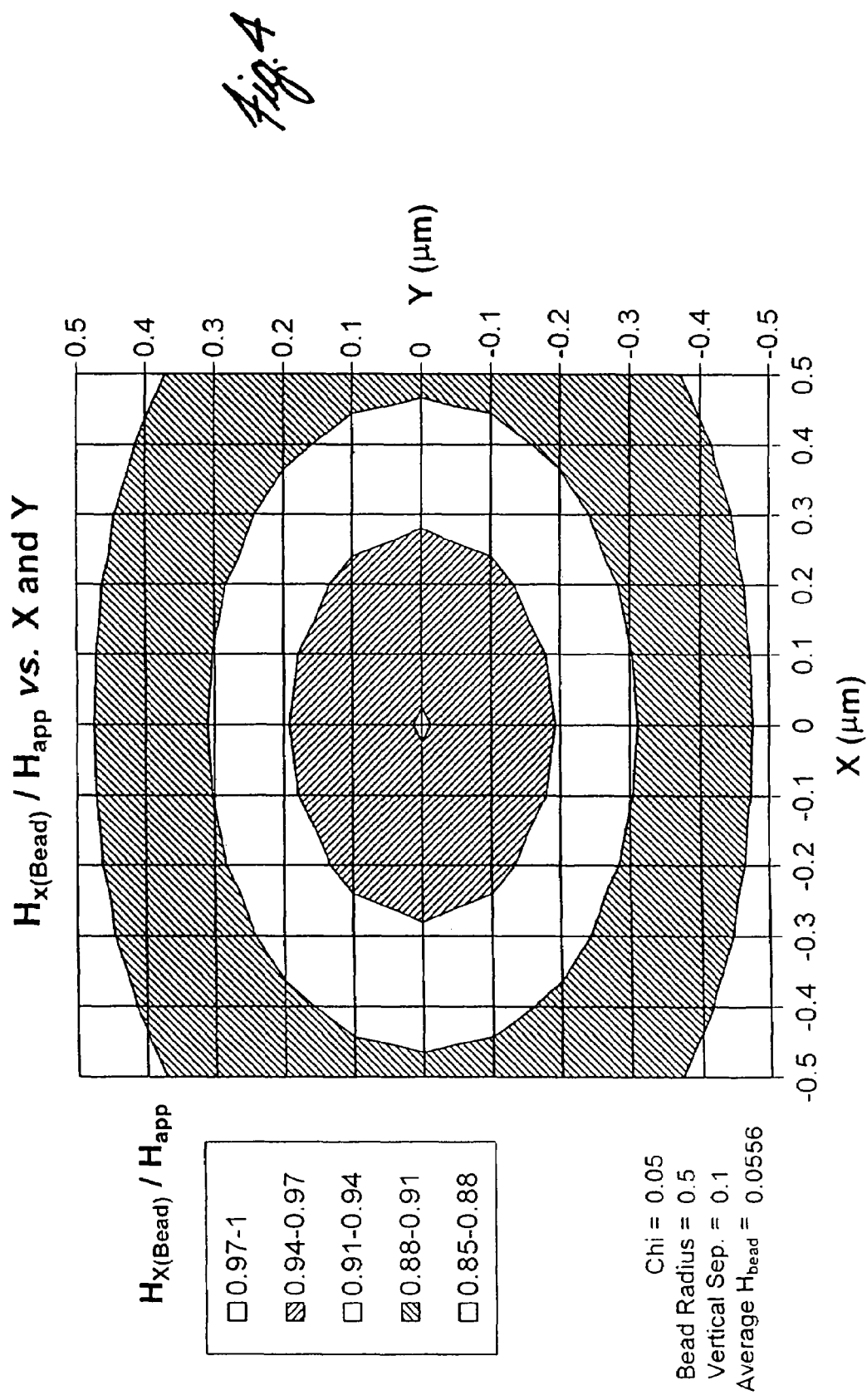
FIG. 4 shows field magnitude value bands for the field of FIG. 3 at a selected plane.

The effect of bead 10 is thus to provide an anomaly in the externally applied field that has the effect of attenuating the total applied field at magnetic field detector structure 11 by about 3%, a change in field value from the value of the externally applied field within the range of detectability of the sensors to be described below. An alternative example provides a fuller representation of this field attenuation situation as shown in FIG. 4 which shows the component parallel to $H_{app}$ of the field from the particle in the plane of magnetic field detector structure 11, this example based on using values of $\chi_m$=0.05, a particle radius of 0.5 μm, and a particle-to-sensor separation of 0.1 μm. But this attenuation effect is limited to the region in the immediate vicinity of bead 10. The magnitude of the distortion to the externally applied field because of the presence of bead 10 drops off approximately as $1/r^3$ in separating from that bead in all directions so that bead 10 must be sufficiently close to magnetic field detector structure 11 if field attenuation in this range is to occur at that structure. Hence, if a single bead is to be detected, it is best to match the size of magnetic field detector structure 11 to the size of bed 10 for maximum resolution.

A suitable arrangement for magnetic field detector structure 11 can be advantageously fabricated using ferromagnetic thin-film materials based on magnetoresistive sensing of magnetic states, or magnetic conditions, thereabout. Such devices may be provided on a surface of a monolithic integrated circuit to provide convenient electrical interconnections between the device and the operating circuitry therefor in the integrated circuit chip.

In the recent past, reducing the thicknesses of the ferromagnetic thin-films and the intermediate layers in extended "sandwich" structures in which the two major surfaces of the intermediate each have thereon an anisotropic ferromagnetic thin-film layer, including those having additional alternating ones of such films and layers, i.e. superlattices, have been shown to lead to a "giant magnetoresistive (GMR) effect" being present. This effect yields a magnetoresistive response which can be in the range of an order of magnitude or more greater than that due to the well-known anisotropic magnetoresistive response.

In the ordinary anisotropic magnetoresistive response, varying differences between the direction of the magnetization vector in the ferromagnetic film and the direction of the sensing current passed through the film lead to varying differences in the effective electrical resistance in the direction of the current. The maximum electrical resistance occurs when the magnetization vector in the film and the current direction are parallel to one another, while the minimum resistance occurs when they are perpendicular to one another. The total electrical resistance in such a magnetoresistive ferromagnetic film can be shown to be given by a constant value, representing the minimum resistance, plus an additional value depending on the angle between the current direction in the film and the magnetization vector therein. This additional resistance follows a square of the cosine of that angle.

As a result, operating external magnetic fields can be used to vary the angle of the magnetization vector in such a film portion with respect to the easy axis of that film portion which comes about because of an anisotropy therein typically resulting from depositing the film in the presence of a fabrication external magnetic field oriented in the plane of the film along the direction desired for the easy axis in the resulting film. During subsequent operation of the device with the resulting film, such operating external magnetic fields can vary the angle to such an extent as to cause switching of the film magnetization vector between two stable states which occur as magnetizations oriented in opposite directions along that easy axis. The state of the magnetization vector in such a film portion can be measured, or sensed, by the change in resistance encountered by current directed through this film portion.

In contrast to this arrangement, the resistance in the plane of a ferromagnetic thin-film is isotropic with respect to the giant magnetoresistive effect, rather than depending on the direction of a sensing current therethrough as for the anisotropic magnetoresistive effect, depends on the cosine of the angle between magnetizations in the two ferromagnetic thin-films on either side of an intermediate layer. In the giant magnetoresistive effect, the electrical resistance through the "sandwich" or superlattice is lower if the magnetizations in the two separated ferromagnetic thin-films are parallel than it is if these magnetizations are antiparallel, i.e. directed in opposing directions. Further, the also present anisotropic magnetoresistive effect in very thin-films is considerably reduced from the bulk values therefor in thicker films due to surface scattering, whereas very thin-films are a fundamental requirement to obtain a significant giant magnetoresistive effect.

In addition, as indicated, the giant magnetoresistive effect can be increased by adding further alternate intermediate and ferromagnetic thin-film layers to extend the "sandwich" or superlattice structure. The giant magnetoresistive effect is sometimes called the "spin valve effect" in view of the explanation that a larger fraction of conduction electrons are allowed to move more freely from one ferromagnetic thin-film layer to another if the magnetizations in these layers are parallel than if they are antiparallel with the result that the magnetization states of the layers act as sort of a valve.

These magnetizations results often come about because of magnetic exchange coupling between the ferromagnetic thin-films separated by the intermediate layers, these intermediate layers typically formed from a nonferromagnetic transition metal. The effect of the exchange coupling between the ferromagnetic thin-film layers is determined to a substantial degree by the thickness of such an intermediate layer therebetween. The effect of the coupling between the separated ferromagnetic thin-film layers has been found to oscillate as a function of this separation thickness between these layers in being ferromagnetic coupling (such that the magnetizations of the separated layers are parallel to one another) and antiferromagnetic coupling (such that the magnetizations of the separated layers are opposed to one another, or antiparallel to one another). Thus, for some separation thicknesses, the layer coupling can be of zero value between extremes of such oscillations.

Exhibiting the giant magnetoresistive effect in a superlattice structure, or in an abbreviated superlattice structure formed by a three layer "sandwich" structure, requires that there be arrangements in connection therewith that permit the establishment alternatively of both parallel and antiparallel orientations of the magnetizations in the alternate ferromagnetic thin-film layers therein. One such arrangement is to have the separated ferromagnetic thin-films in the multilayer structure be antiferromagnetically coupled but to a sufficiently small degree so that the coupling field can be overcome by an external magnetic field.

Another arrangement is to form the ferromagnetic thin-film layers with alternating high and low coercivity materials so that the magnetization of the low coercivity material layers can be reversed without reversing the magnetizations of the others. A further alternative arrangement is to provide "soft" ferromagnetic thin-films and exchange couple every other one of them with an adjacent magnetically hard layer (forming a ferromagnetic thin-film double layer) so that the ferromagnetic double layer will be relatively unaffected by externally applied magnetic fields even though the magnetizations of the other ferromagnetic thin-film layers will be subject to being controlled by such an external field.

One further alternative arrangement, related to the first, is to provide such a multilayer structure that is, however, etched into strips such that demagnetizing effects and currents in such a strip can be used to orient the magnetizations antiparallel, and so that externally applied magnetic fields can orient the magnetizations parallel. Thus, parallel and antiparallel magnetizations can be established in the ferromagnetic thin-films of the structure as desired in a particular use. Such a structure must be fabricated so that any ferromagnetic or antiferromagnetic coupling between separated ferromagnetic films is not too strong so as to prevent such establishments of film magnetizations using practical interconnection arrangements.

A magnetic field sensor suited for fabrication with dimensions of a few microns or less can be fabricated that provides a suitable response to the presence of very small external magnetic fields and low power dissipation by substituting an electrical insulator for a conductor in the nonmagnetic layer. This sensor can be fabricated using ferromagnetic thin-film materials of similar or different kinds in each of the outer magnetic films provided in a "sandwich" structure on either side of an intermediate nonmagnetic layer which ferromagnetic films may be composite films, but this insulating intermediate nonmagnetic layer permits electrical current to effectively pass therethrough based primarily on a quantum electrodynamic effect "tunneling" current.

This "tunneling" current has a magnitude dependence on the angle between the magnetization vectors in each of the ferromagnetic layers on either side of the intermediate layer due to the transmission barrier provided by this intermediate layer depending on the degree of matching of the spin polarizations of the electrons tunneling therethrough with the spin polarizations of the conduction electrons in the ferromagnetic layers, the latter being set by the layer magnetization directions to provide a "magnetic valve effect". Such an effect results in an effective resistance, or conductance, characterizing this intermediate layer with respect to the "tunneling" current therethrough.

There are many types of magnetoresistive material that can be used. A sandwich type (e.g. 35A NiFeCo/15 CoFe/Cu 35/15 CoFe/35 NiFeCo) or a pinned sandwich (e.g. 35A NiFeCo/15 CoFe/Cu 35/40 CoFe/100 IrMn, also called a spin valve) are useful arrangements. They have lower saturating fields the structures described for use below, and so are more sensitive, but also more likely to be saturated by any bead magnetizing fields. Anisotropic Magnetoresistive (AMR) films can also be patterned into such devices. The key for all of these will be to get the beads close to the sensitive layer or layers, and to magnetically bias the magnetoresistors such that they give maximum sensitivity to the presence of the beads. Another enhancement to the sensing material is to give it "hard edges" by oxidizing the edges, pinning them with some antiferromagnetic material, or constructing them so that the two magnetic layers contact each other at the edge of the resistor stripe. Resistors prepared this way will have lower hysteresis in the range of magnetic field magnitudes relevant for the assay.

The GMR magnetoresistors typically used here are formed of a succession of thin, alternating magnetic and nonmagnetic metallic layers having an electrical resistance that is a function of an external magnetic field. This resistance, as stated above, varies with the angle $\theta$ between the magnetizations of adjacent magnetic layers with a sin $\theta$ dependance, and a typical change from a minimum (i.e., magnetic layers are aligned in parallel) to maximum (i.e., when magnetic layers are aligned antiparallel) resistance is ~10% of the minimum value. The thin succession of layers is fashioned into sensors as long, thin, rectangular structures but with pointed ends. The observed resistance is then proportional to the length and inversely proportional to the width. A typical sheet resistance is 10 ohms/□. Consequently, such a typical magnetoresistor with a respective width and length of 0.5 and 5.0 microns (10 squares) would have resistance of 100 ohms under parallel magnetic layer magnetizations that increases to 110 ohms (10%) when under antiparallel magnetic layer magnetizations.

The preceding last example, however, assumes instead for convenience that a 1 μm×1 μm GMR detector is positioned directly beneath paramagnetic label bead 10 so that this bead is situated above the upper surface of structure 11 in the z direction. Such a detector would typically have a current therethrough of 5 mA, and a 10 Ω to 11 Ω resistance change corresponding to $H_{app}$ ranging from 200 Oe to 0 Oe. This represents the 10% resistance change over 200 Oe as indicated in Figure J. The detector voltage, then, changes at a rate of 25 μV/Oe. The maximum $H_{app}$ possible without saturating the sensor is 200 Oe. The field attenuation from the bead modeled above is, on average, 0.05 times the $H_{app}$. Though the total resistance change will be slightly less than the average field change due to current redistribution within the GMR sensor, assume for now that the net resistance change is exactly proportional to the average field change. Hence, the maximum total signal field is 10 Oe (0.05×200 Oe). The voltage "signal" from the bead is then 250 μV.

The noise of the detector has two main components: thermal noise and current dependent 1/f noise. The thermal (Johnson) noise for a 10 Ω resistor is 0.4 nV/√. The detector's intrinsic 1/f noise will typically be two orders of magnitude higher than the thermal noise at 1 Hz, and have a corner frequency at 10 kHz. Assuming a 1 Hz measurement frequency, the total noise will be dominated by the 1/f noise, and be about 40 nV/√. So the signal to noise ratio at 1 Hz with a 1 Hz bandwidth is 250 μV/40 nV=6250:1. While this simple calculation ignores engineering challenges that must be addressed to fully use the available signal, it is clear that detection of a single 1 μm diameter bead with a 1 μm×1 μm GMR detector is not limited by fundamental signal to noise issues.

Figure 5:
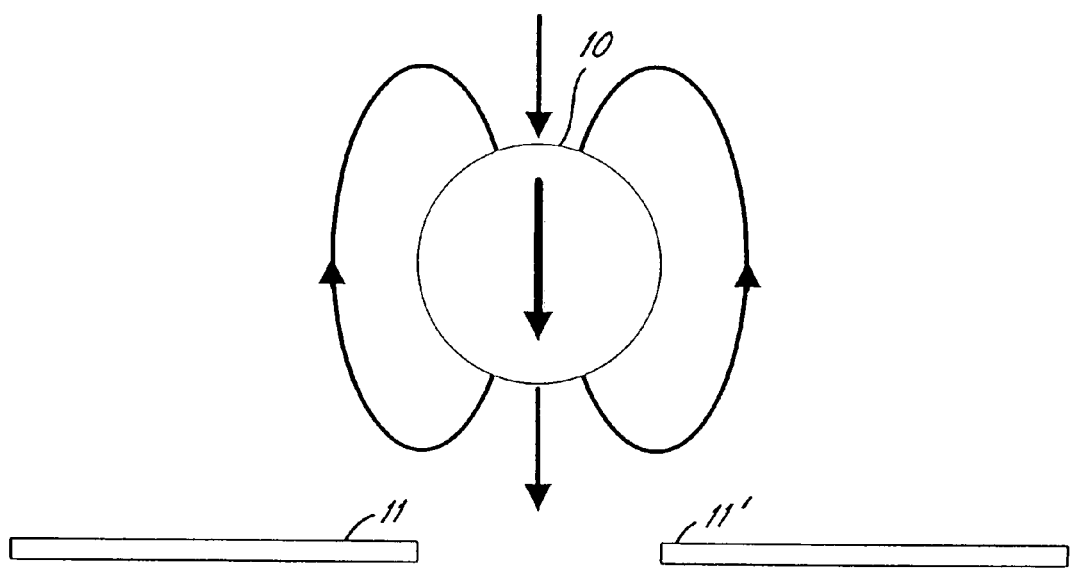
FIG. 5 shows an alternative magnetizable sphere based magnetic response field schematic over a structure.

The relative positional arrangement in FIG. 2 of bead 10 and GMR magnetic field detector structure 11, and the relative orientation of the externally applied magnetic field, can be varied. One variation of the externally applied magnetic field relative orientation is to apply such a field normal to the plane of GMR detector structure 11 as shown in FIG. 5. GMR detector structure 11 is about 1000 times more difficult to magnetize in the direction normal to its major surface than in a direction parallel thereto, and so a much larger magnetizing field can be applied to bead 10 and that structure without saturating the GMR magnetoresistors therein. Here, magnetic field detector structure 11, rather being shown by itself with bead 10 directly thereover, is shown over a space between that structure and another GMR magnetic field detector structure, 11'.

The use of multiple magnetoresistors in GMR magnetic field detector 11 permits measurement circuit advantages including use of a differential detection, e.g. a bridge circuit detector, arrangement. Although a bead detection site can be provided with only one magnetoresistor as shown in FIG. 2, a bridge circuit having two or more magnetoresistors therein offers several benefits including rejection of common mode noise, and provision of first order temperature compensation. In such a bridge circuit, one or more of several GMR magnetoresistors provided therein are exposed to possible magnetic field anomalies due the possible presence of bead 10 while the remaining magnetoresistors are not so exposed, or are instead exposed to fields in the opposite direction.

Figure 6:
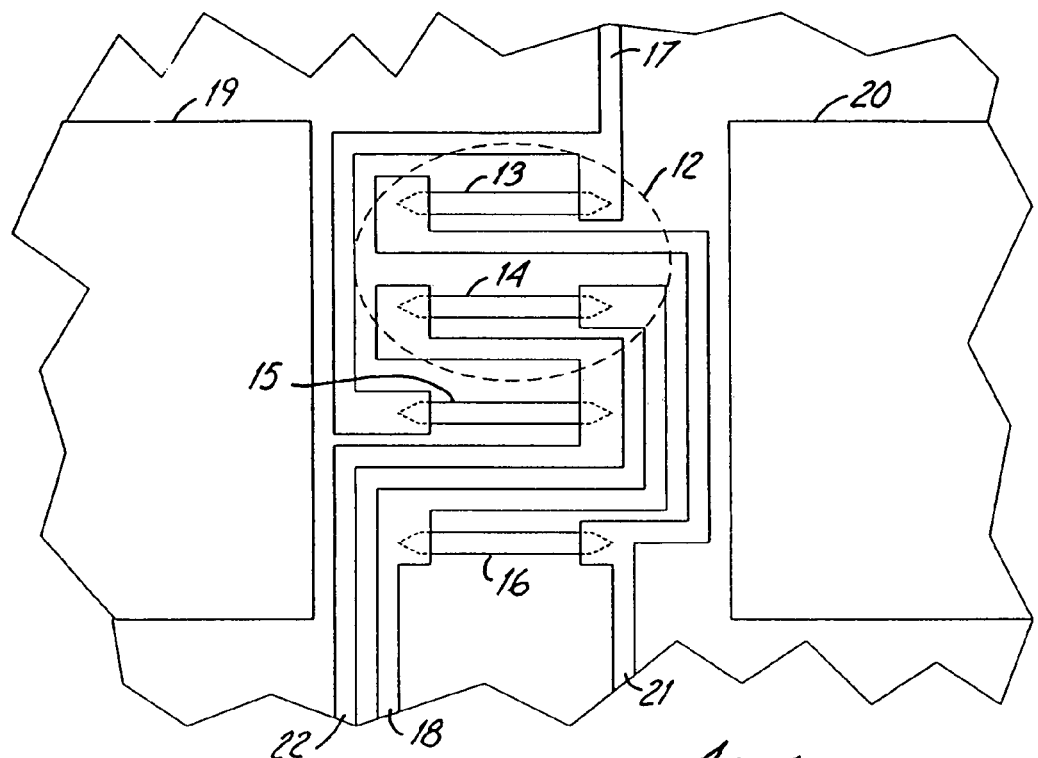
FIG. 6 shows a detector device portion embodying the present invention.
Figure 7:
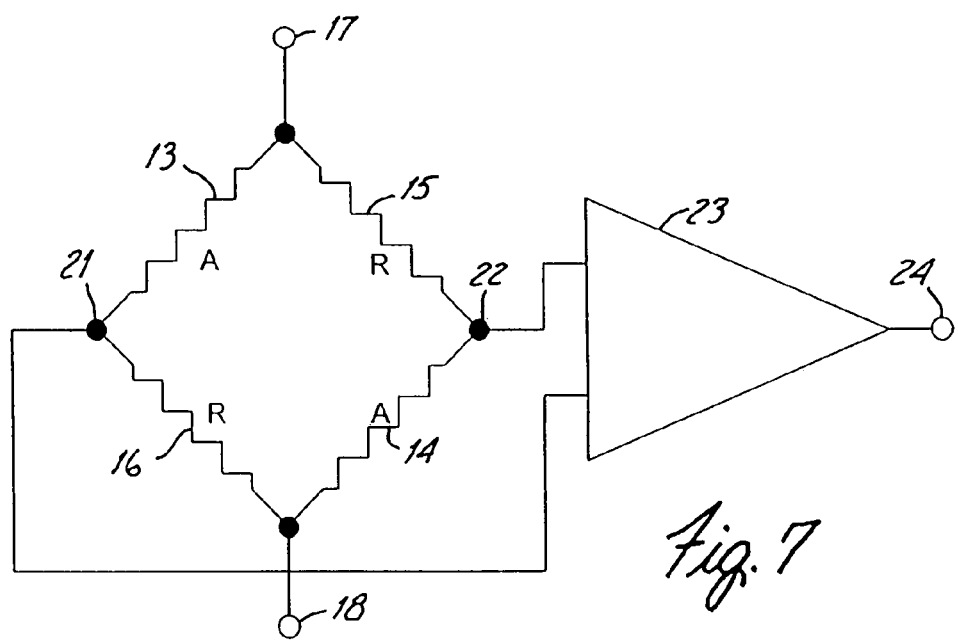
FIG. 7 shows an electrical schematic diagram providing a representation of FIG. 6, FIGS. 8 and 9 show layer diagrams of a detector device portion embodying the present invention.

One such example is shown in FIGS. 6 and 7. A single bead detection site, 12, formed by the presence of a binding molecule coating, is provided having four GMR magnetoresistors, 13, 14, 15 and 16, as individual sensors electrically connected together the metal interconnections shown in a Wheatstone bridge arrangement between metal interconnections voltage supply terminals, 17 and 18, and located between two flux concentrators, 19 and 20, to be described below. Site 10 is provided so that one pair (active) of magnetoresistors, that is, 13 and 14, are in opposite legs of the bridge circuit and subject to the field anomaly introduced by the presence of bead 10 while the other pair (reference) formed of magnetoresistors 15 and 16 is not so subjected even they are also subjected to the externally applied field. The signal developed across the bridge circuit is provided between two metal interconnections signal terminals, 21 and 22, and provided to the signal inputs of a differential amplifier, 23, providing a corresponding differential output signal at its output, 24.

Keeping these two pairs of magnetoresistors distinguishable as active magnetic field anomaly sensing magnetoresistors and reference magnetic field sensing magnetoresistors during an assay can be accomplished using one or another of several techniques. The simplest way is to provide a covering of a suitable kind such that no bead ever reaches a position sufficiently close to the reference magnetoresistors to magnetically affect them. Alternatively, the detection site can be fabricated, or subsequently modified, so that few or no particles will able to adhere to a surface of, or a surface near, the reference magnetoresistors. In addition, or instead, a passivation layer over the detector surface (the upper or final layer shown over all else) can be kept thick over the reference magnetoresistors as in the layer diagram of FIG. 8 to substantially separate bead 10 therefrom but kept thin over the active magnetoresistors (the upper or final two layers removed over structure 11 with or without binding molecule coating 12 provided there) as shown in the layer diagram of FIG. 9 to allow bead 10 to approach closely.

Figure 9:
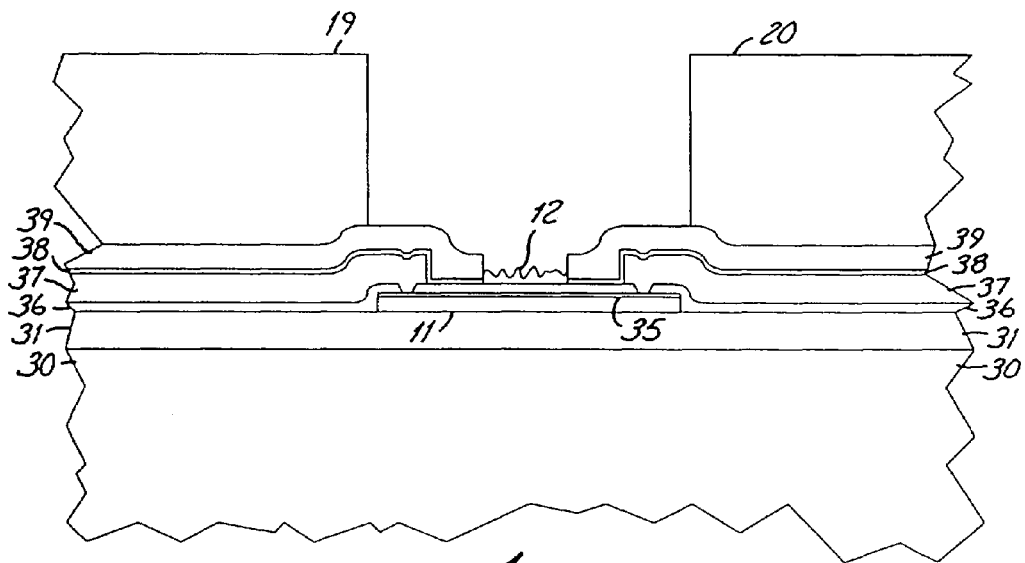
Figure 10:
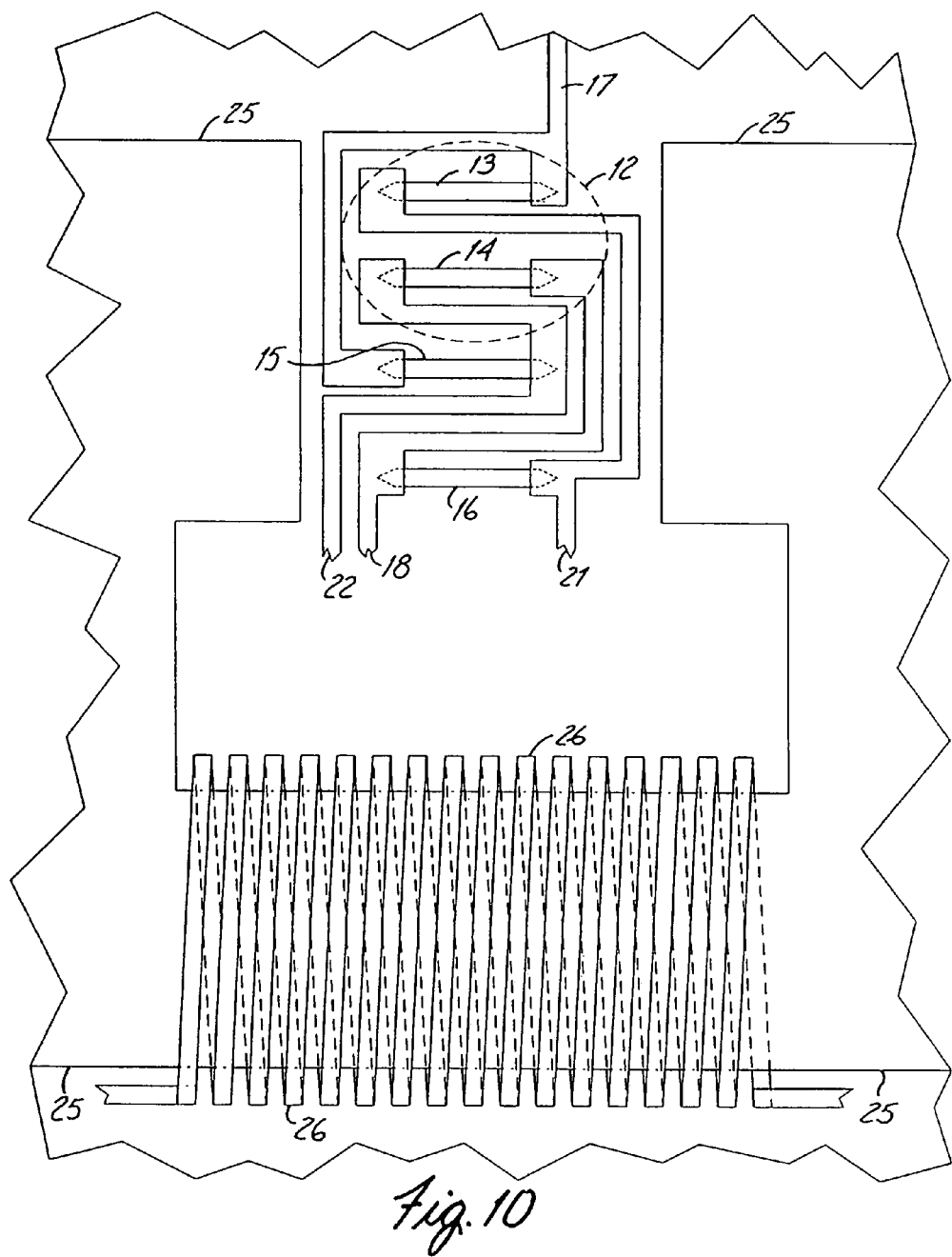
FIG. 10 shows a detector device portion embodying the present invention.

Flux concentrators 19 and 20 in the form of permeable material masses can be incorporated into a bridge circuit detection arrangement to concentrate externally applied magnetic fields in and about the active magnetoresistors, as shown in FIGS. 6 and 9, or a flux concentrator, 25, can be provided to increase and guide magnetic fields developed in the detector itself through providing current through a conductor coil, 26, formed thereabout as shown in FIG. 10. In each instance, both the active pair and the reference pair of magnetoresistors are shown positioned in the gap between two such concentrating flux concentrators, or in the gap between the two ends of an enhancing and guiding flux concentrator, so that they all will be immersed in substantially the same concentrated externally applied magnetic field.

In such an arrangement, the flux concentrator or concentrators are simply acting as a multiplier of the externally applied magnetic field. The multiplication factor is approximately [concentrator length]/[concentrator separation gap]. Alternatively, the reference magnetoresistors can be positioned underneath the flux concentrators. They will in such a position experience a much smaller net field (they are substantially shielded from the applied field) than the active magnetoresistors positioned in the concentrator gap (the common mode field rejection is then lost) but they will require no space to be provided for them in the gap.

Figure 8:
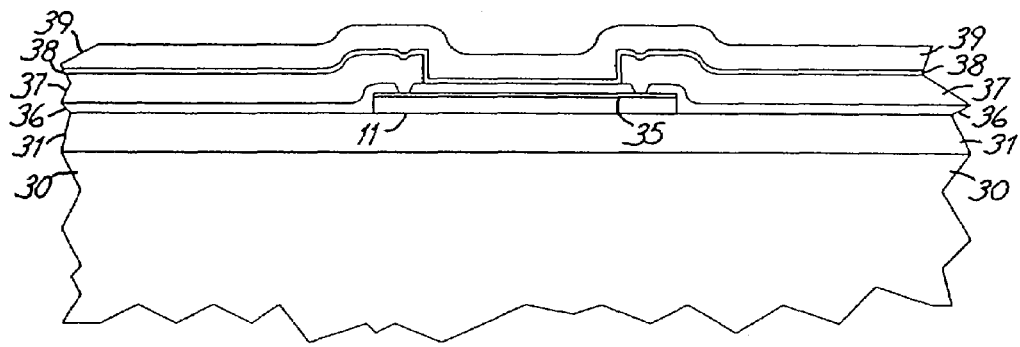

The methods used to fabricated structures like those shown in FIGS. 8 and 9 are based on well known semiconductor device fabrication processes. Two alternative processes will be described, the choice of which depends on whether the resulting devices are to have interconnection metal provided above or below the GMR magnetic field detector structure. If the interconnection metal is to be provided below the GMR magnetic field detector structure, a Si based wafer, 30, which may have monolithic integrated circuitry therein, has a 200 nm layer of substrate $Si_3N_4$, 31, supported thereon, on which a 1.5 μm layer of Al is first deposited. This Al layer is patterned using standard photolithography and a reactive ion etch (RIE) to form what will become the interconnections, 32, for the magnetic field detector, or assay, circuit. A 2.5 μm (must be at least as thick as the previous Al layer) thick layer of $Si_3N_4$ is deposited over the patterned Al. Then, the resulting surface is planarized using chemical mechanical polishing (CMP). The Al interconnections are exposed during the CMP, so that the resulting surface of the wafer has both Al and a $Si_3N_4$ base, 33, in it. Both materials are smooth. The GMR magnetic field detector structure material is then deposited.

The succession of alternating magnetic and nonmagnetic metallic thin-film layers in the GMR magnetic field detector structure is formed in a vacuum deposition system using rf diode sputtering. The succession thickness is 10 nm to 40 nm, depending upon the particular structure chosen for use. The thicknesses of individual layers within the succession are controlled to tenths of nanometers. The GMR succession is followed by providing thereon a 10 nm CrSi etch stop layer on which is further provided a 40 nm $Si_3N_4$ mask layer. The $Si_3N_4$ mask layer is patterned using standard photolithography and an RIE etch. The GMR magnetic field detector structure+etch stop succession is then etched through the resulting $Si_3N_4$ mask using an ion mill to leave the GMR magnetic field detector structure 11 magnetoresistors, 34. Most or all of the $Si_3N_4$ mask is etched away in the ion mill, and at least some or all of the CrSi layer, 35, below this mask remains on these magnetoresistors. At this point, the GMR magnetic field detector structure 11 magnetoresistors and Al interconnections are complete and can be tested.

Figure 11:
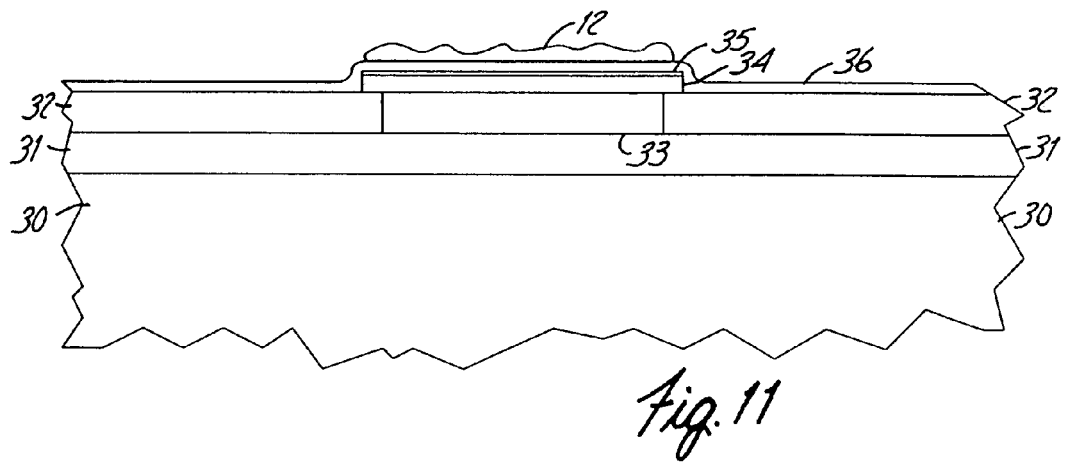
FIG. 11 shows a layer diagram of a detector device portion embodying the present invention.

The GMR magnetoresistors and the Al interconnections are then passivated if desired by providing thereover a thin layer of $Si_3N_4$ as a passivation layer, 36. The required thickness of this passivation layer depends upon two things, the step height of the GMR magnetoresistors above the base layer therebelow, and the standoff voltage required between the GMR elements and the bead samples that will be present above the passivation. If some passivation is required and the voltage requirements are minimal, though non-zero (<10 Volts), the passivation layer minimum thickness limitation will be the first requirement for topological coverage of the GMR step edge. A rule of thumb is to use a passivation layer thickness equal to that of the step being covered, although less is possible. A passivation layer thickness of 10 nm is typically sufficient. Such a passivation layer provides a nominal standoff voltage of about 1000 Volts/μm, so a 10 nm passivation will nominally provide 10 V. The resulting detector is shown in FIG. 11 with binding molecule coating 12 provided thereon when desired over GMR magnetic field detector structure 11 magnetoresistors 34.

If the interconnection metal is to be provided above the GMR magnetic field detector structure, on the other hand, the structures of the layer diagrams in either of FIGS. 8 and 9 can be fabricated. In this situation, the succession of alternating magnetic and nonmagnetic metallic thin-film layers in the GMR magnetic field detector structure is deposited directly upon substrate $Si_3N_4$ layer 31 on Si wafer 30 as above. An 10 nm CrSi etch stop layer plus a $Si_3N_4$ masking layer of 40 nm thickness is deposited, and then photolithography and RIE are used to pattern the $Si_3N_4$ to form an etching mask, followed again by use of an ion mill to etch the GMR magnetic field detector structure+etch stop succession thereby leaving the GMR magnetic field detector structure 11 magnetoresistors. Again, most or all of the $Si_3N_4$ mask is gone after this milling, and most or all of CrSi etch stop layer 35 under this mask remains on these magnetoresistors.

Thin $Si_3N_4$ passivation layer 36 is then deposited, serving here as an inner passivation layer, and passageways, or vias, to the GMR magnetic field detector structure 11 magnetoresistors are etched in inner passivation layer 36 using RIE. A relatively thick Al (~1 μm) layer is next deposited and patterned using photolithography and RIE, so that interconnections, 37, are made for the GMR magnetic field detector structure 11 magnetoresistors. The Al needs to be thick so that the lead resistance is low compared to the resistance of these magnetoresistors. Exposed surfaces of aluminum interconnections 37 and $Si_3N_4$ passivation layer 36 then have deposited thereon a 10 nm aluminum nitride (AlN) layer, 38, for its adhesion properties followed by a 1.5 μm $Si_3N_4$ layer, 39, which together form the outer passivation for the device. FIG. 8 shows a layer diagram of the resulting structure at this point of the fabrication process which leaves an outer passivation layer so thick that bead 10 thereon over GMR magnetic field detector structure 11 magnetoresistors would have little magnetic effect on those reference magnetoresistors or relatively less magnetic effect on actively sensing magnetoresistors.

However, to provide actively sensing magnetoresistors also, photolithography and RIE are used to remove the $Si_3N_4$ portion of the outer passivation layer from selected areas or some portion of that layer thereover. Such areas include those over bonding pads for external wiring and, of course, those over certain magnetoresistor sites where enhanced sensitivity to magnetic particles is desired. Material milling in an ion mill step is used to remove the exposed AlN layer in these regions in a controlled way, leaving nearly the full thickness of the underlying inner $Si_3N_4$ passivation layer, or somewhat less if desired. FIG. 9 shows the layer diagram of the result upon the completion of these steps in the fabrication process if binding molecule coating 12 and flux concentrators 19 and 20 are ignored.

Flux concentrators 19 and 20 can be added at this point for amplifying externally applied fields, or coil 26 and flux concentrator 25 can be added at this point for guiding on-chip fields. A photoresist plating mold is formed, and permalloy is electroplated into the mold to a thickness of about 15 μm to form flux concentrators 19 and 20. FIG. 9 shows the structure resulting to this point in the fabrication process if binding molecule coating 12 is again ignored.

There are many methods to provide binding molecule coating 12, i.e. of preparing the assay probe region, the particulars of which depend upon the intended purpose of the assay. One method to create probes for a DNA hybridization assay is described in the following.

The resulting structure after the flux concentrators are completed is coated with gold using a lift-off mask that leaves gold over large portions of the chip, but such that it does not short different magnetoresistor interconnections together. Then spots of reagents containing thiolated DNA oligomers are dispensed over the intended assay probe region using a Sapphire-tipped Rapidograph pen. In order to keep the non-probe regions inert, the chip surface is also treated with thiolated PEG (O-(2-mercaptoethyl)-o'-methyl-polyethylene glycol 5000. Such a material can be used to complete the device shown in FIG. 9 in providing coating 12 shown there.

Figure 12:
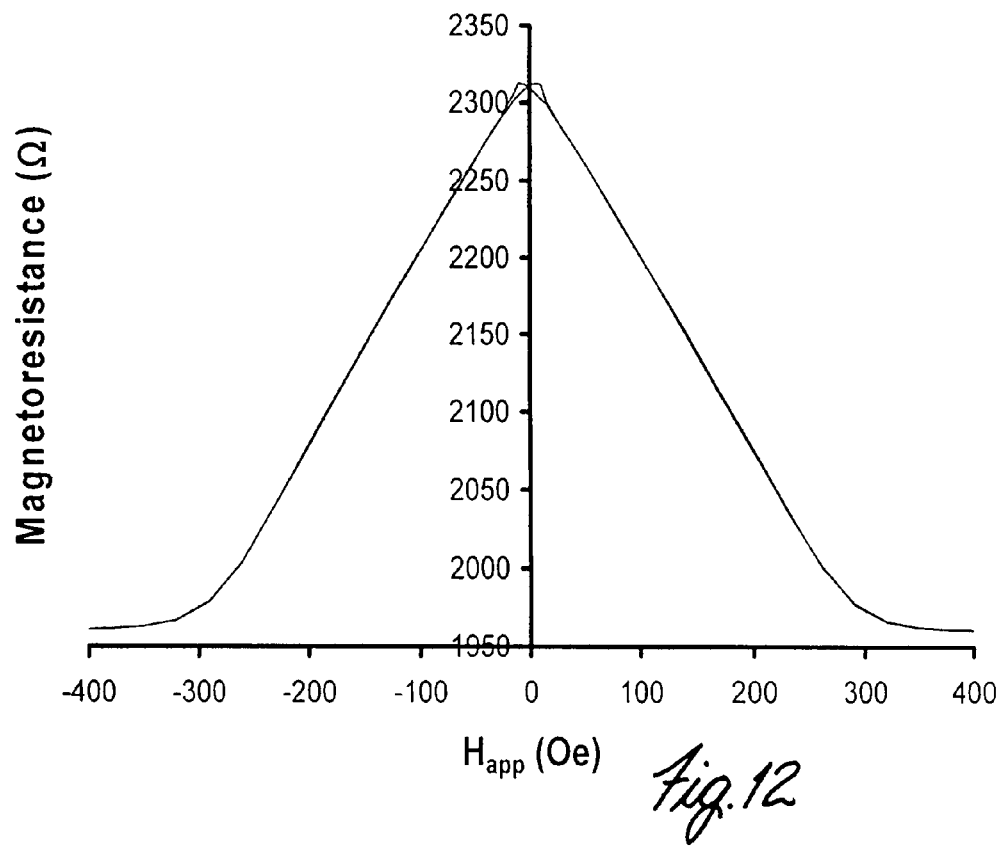
FIG. 12 shows a graph having a plot representing performance of a component used with the present invention.

The response of a typical GMR magnetic field detector structure magnetoresistor to an external magnetic field is unipolar, linear, and saturates in fields ranging from tens of Oe to a few hundreds of Oe, depending upon the particular magnetic design. A plot of the observed resistance vs. externally applied magnetic field strength for a typical multilayer GMR magnetic field detector structure magnetoresistor is shown in FIG. 12. The presence of a bead 10 is then detected by observing a change in the resistance due to the external field experienced by the magnetoresistor.

Detecting a single magnetizable bead with GMR magnetic field detector structure magnetoresistors at a binding molecule coated assay surface, as essentially set out above, is typically insufficient in view of the overall assay signal-to-noise ratio being proportional to the number of capture sites at the assay surface, i.e. proportional to the square root of the assay surface area over which such sites are provided, assuming a random areal distribution of "noise events". Assay "noise events" include situations like beads sticking where they are not supposed to be sticking in the detection scheme (non assay-specific adhesion, leading to artificially high magnetic signal) and other kinds of particles (other than beads) sticking to detection sites in place of beads (contaminants, for instance, leading to artificially low magnetic signal).

However, individual assay surface sizes on the order of 10 to 1000 μm in diameter often result if formed by techniques that are not lithographically based such as forming the assay surface sites by "spotting" the chip with fluid using a fine plotter-type device or a tiny metal point dipped in an appropriate solution to provide the binding molecule coating. These techniques result in spot sizes much larger than 1 μm. Lithographic techniques, instead, can result in much smaller individual effective detectors over the assay surface.

Thus, assay surfaces that are much larger than a typical bead, say a 50 μm sided square, lead to a desire to measure the surface concentration of beads across the entire surface, or detection site, as accurately as possible. This implies having a detector arrangement with an active region covering as much of the site as possible, and which provides a response to beads captured at the site that is uniform across the site. A GMR magnetic field detector structure magnetoresistor arrangement having multiple effective individual detectors can be provided across such a assay surface, or detection site, by having several individual GMR magnetic field detector structure magnetoresistors electrically connected together in series.

Figure 13:
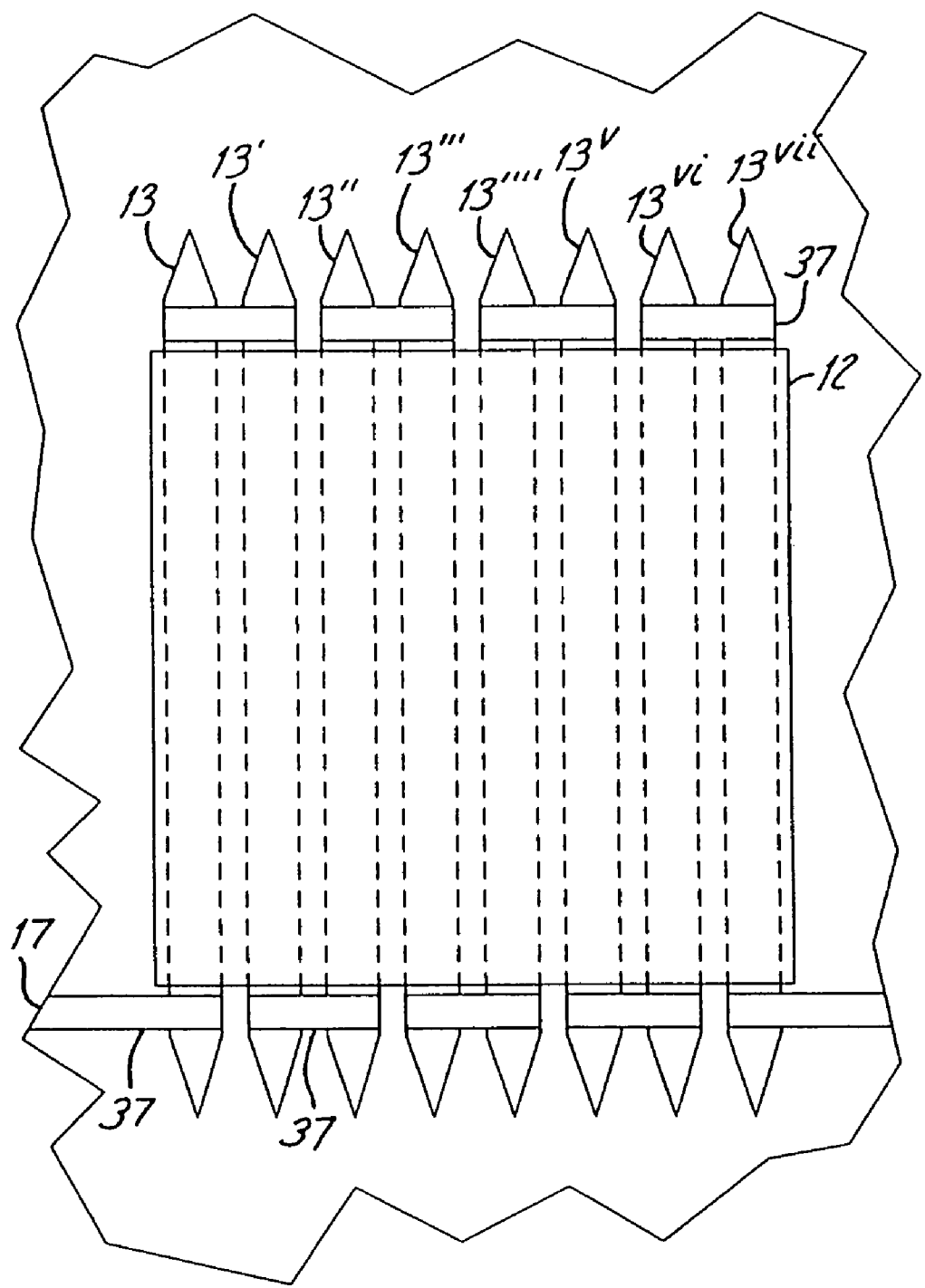
FIGS. 13, 14 and 15 show detector device portions embodying the present invention.

FIG. 13 shows a top view of such a detector arrangement in a portion of a device formed on an integrated circuit under a square binding molecule coating forming detection site 12 in which the individual GMR magnetic field detector structure magnetoresistors are each approximately 4 μm wide, separated by 2 μm, and connected together using Al metal interconnections 37 formed over the top of the series connected magnetoresistors. Passivation layers and any flux concentrators used are omitted from this view for clarity. These magnetoresistors are individual sensors like the magnetoresistors in FIG. 6 and so designated 13, 13', 13", 13'", 13"", 13$^v$, 13$^{vi}$ and 13$^{vii}$ in representing an active group of magnetoresistors. The "active region", or detection site 12, is a square 50 μm on a side that is effectively defined by the existence of the binding molecule coating "assay surface" and possibly other construction features such as thinned sensor passivation, etc.

In situations where a full Wheatstone bridge circuit is desired to be used, the same assay surface can be monitored by two series connected, interleaved GMR magnetic field detector structure magnetoresistor groups connected as shown in FIG. 14 for again a portion of a detector device formed on an integrated circuit with some layers omitted for clarity. These groups are again taken as like the magnetoresistors in FIG. 6 and so designated 13, 13', 13" and 13'" for one group of active resistors, and designated 14, 14', 14" and 14'" for the other group of active resistors. The gap between two adjacent magnetoresistors is ideally as small as possible to maximize surface coverage, but is limited in coverage by practical lithographical spacing considerations. The width of each of the magnetoresistors can vary over a wide range, from the narrowest that can be fabricated (<0.5 μm) in the best resolution fabrication process to as wide as the entire assay site if only one or two magnetoresistors are to be used. The length-to-width ratio of each of the magnetoresistors is to be such that the resistance total of the groups satisfies detection circuit criteria. For example, some preamplifiers operate best with a source impedance of about 1 kΩ which requires 100 squares of 10 Ω/square material. The resistor in FIG. 13 has 8 legs, each 4 μm×50 μm=12.5 squares=125 Ω for a total of 1 kΩ.

The width of an individual magnetoresistor is also important because the most sensitive region of such a magnetoresistor is in the interior thereof because the edges thereof are magnetically relatively stiff in resistor rotation of the magnetization in those regions. Wider resistors, in so having a proportionally larger sensitive region, will thus be more sensitive. On the other hand, wider resistors require more current to generate the same voltage signal because of reduced resistance. Too much current can generate excess heat which may disturb or destroy the coating forming the assay surface or affect the test in other ways.

The system sensitivity to a single bead is enhanced by using multiple GMR magnetic field detector structure magnetoresistors with respect to such a bead so that more than one of those magnetoresistors is affected by the magnetic field anomaly introduced by the presence of a bead. Thus, rather than having the bead come to a position directly above a magnetoresistor, the bead would instead be directed to a position between two adjacent magnetoresistors, or even in the area between four such magnetoresistors. A channel can be provided between each member of a pair of magnetoresistors, or a hole could be provided in the area between four magnetoresistors, in which the beads would be more likely to be captured, and in which the binding molecule coating forming the assay surface would be placed. Such an arrangement is shown in the top view in FIG. 15 in which a bridge circuit is shown formed in a portion of the detector arrangement provided on a monolithic integrated circuit having detection site 12 located between active magnetoresistors 13 and 14 where each will experience the magnetic field anomaly introduced by the presence of a bead 10 bound to site 12 while more remotely located reference magnetoresistors 15 and 16 will not.

Figure 15:
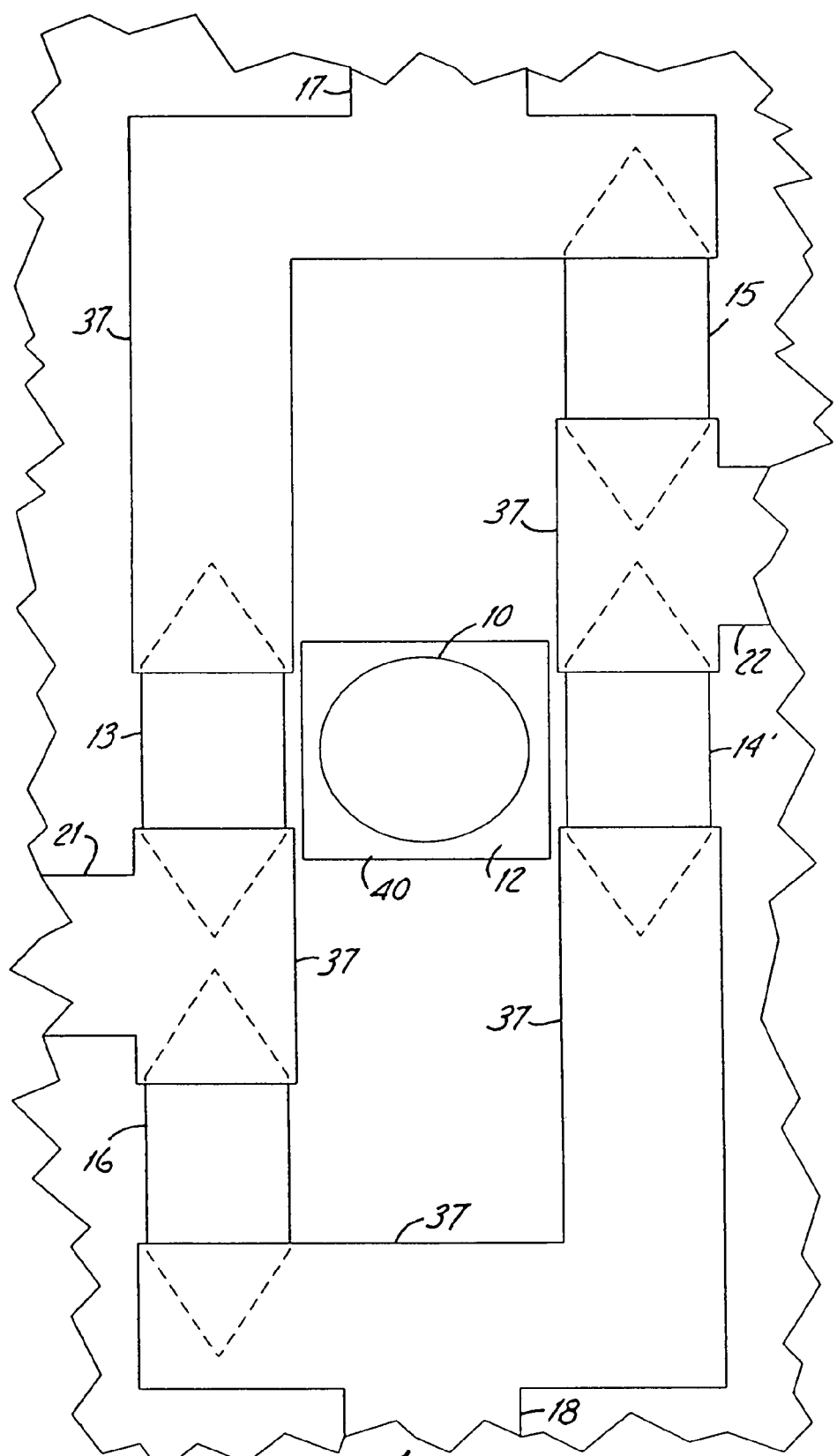
Figure 16:
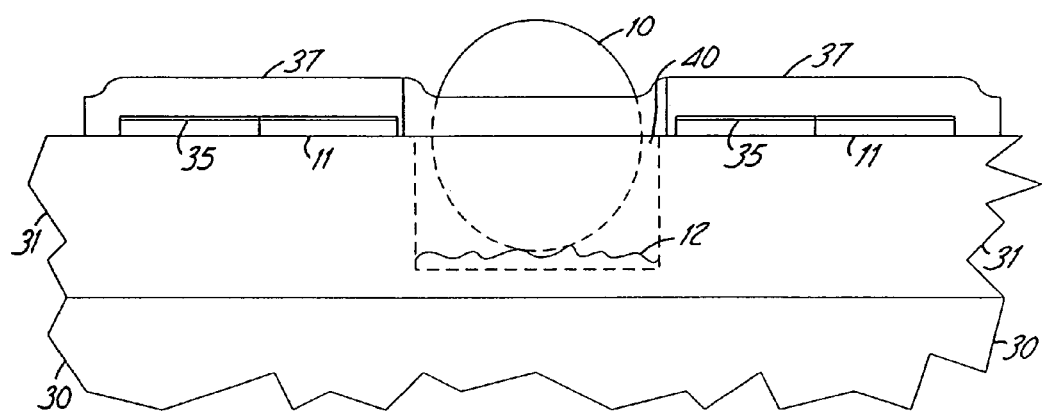
FIGS. 16 and 17 show layer diagrams of a detector device portion embodying the present invention.

The depth of these channels or holes, 40, should be such that the center of the bead is level with the magnetoresistors in the vertical direction as is shown in FIG. 16 which is a portion of a layer diagram of the device portion shown in FIG. 15 and an enhancement of the structure shown in FIG. 9. This arrangement is advantageous when using an externally applied excitation magnetic field that is directed parallel to the major surfaces of the magnetoresistors as in FIG. 15 which could be alternating direction fields. The response magnetic field from the bead would be similarly directed, and the resulting poles of the bead would be very close to the magnetoresistor edge for properly chosen magnetoresistor dimensions. The alternative situation for the arrangement of FIG. 15 is to rely just on the binding molecule coating to keep a bead 10 between magnetoresistors 13 and 14 as shown in FIG. 17.

Word lines, or structures like them, can be used to generate such externally applied fields on-chip that either supplement or eliminate off-chip magnetic field generating. Permeable mass flux keepers can be used to direct the flux from the lines and from the beads. Use of a buried word line would allow the beads to be close to the magnetoresistors as does the use of buried connectors as shown in FIG. 11. Alternatively, the externally applied excitation magnetic fields could be directed perpendicularly to the major surfaces of the magnetoresistors but then off-chip magnetic field generating is likely to be needed.

Figure 17:
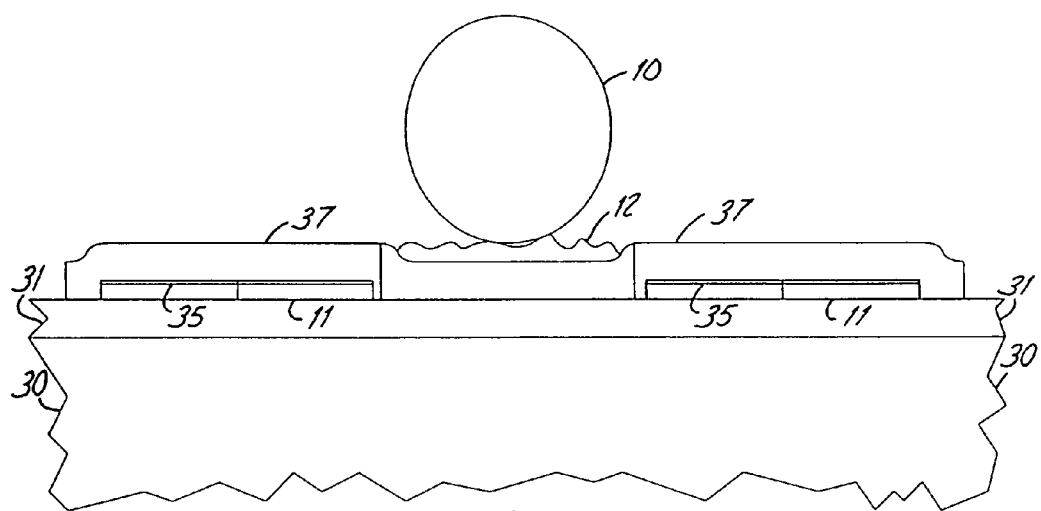
Figure 18:
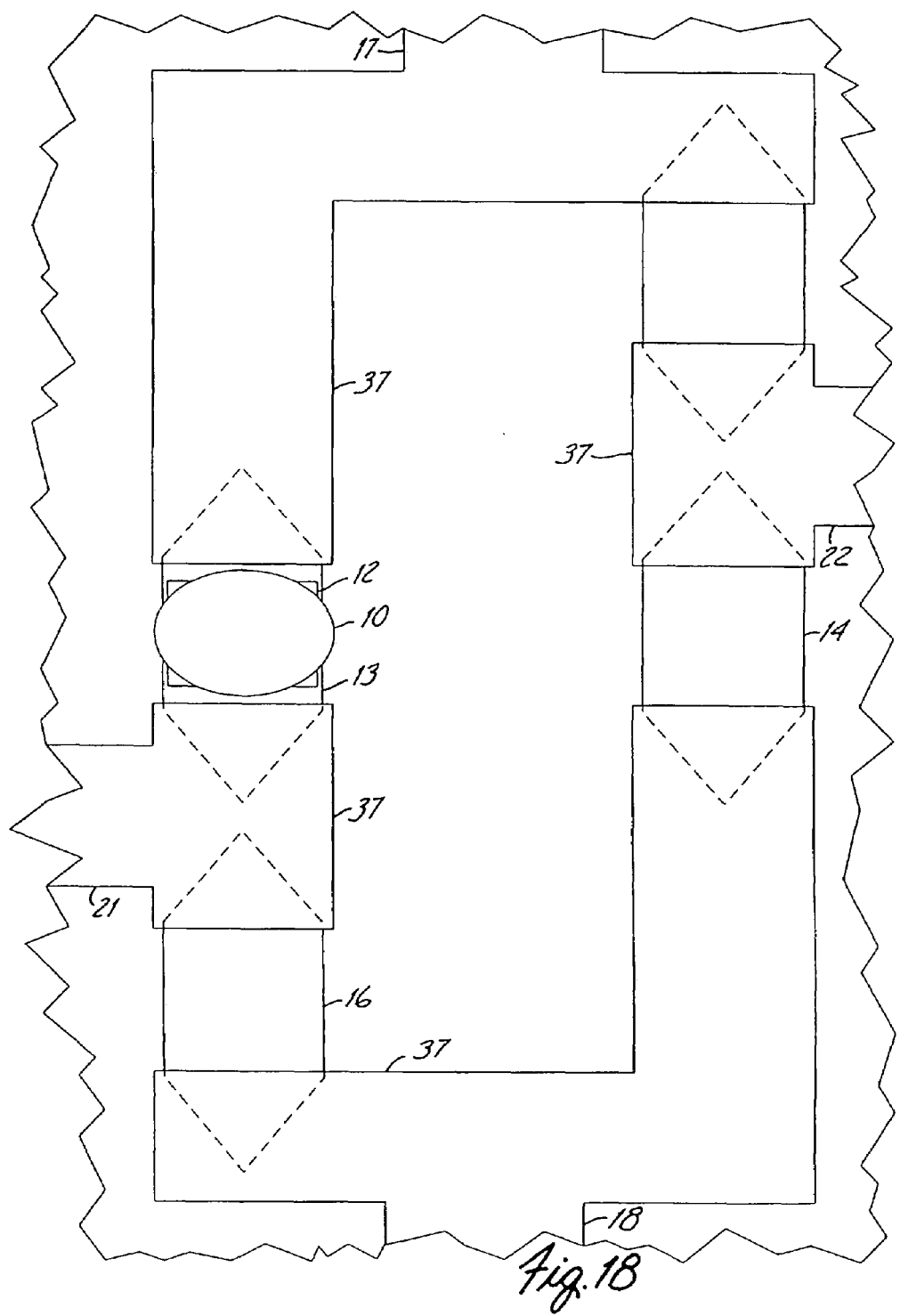
FIGS. 18, 19 and 20 show detector device portions embodying the present invention.
Figure 19:
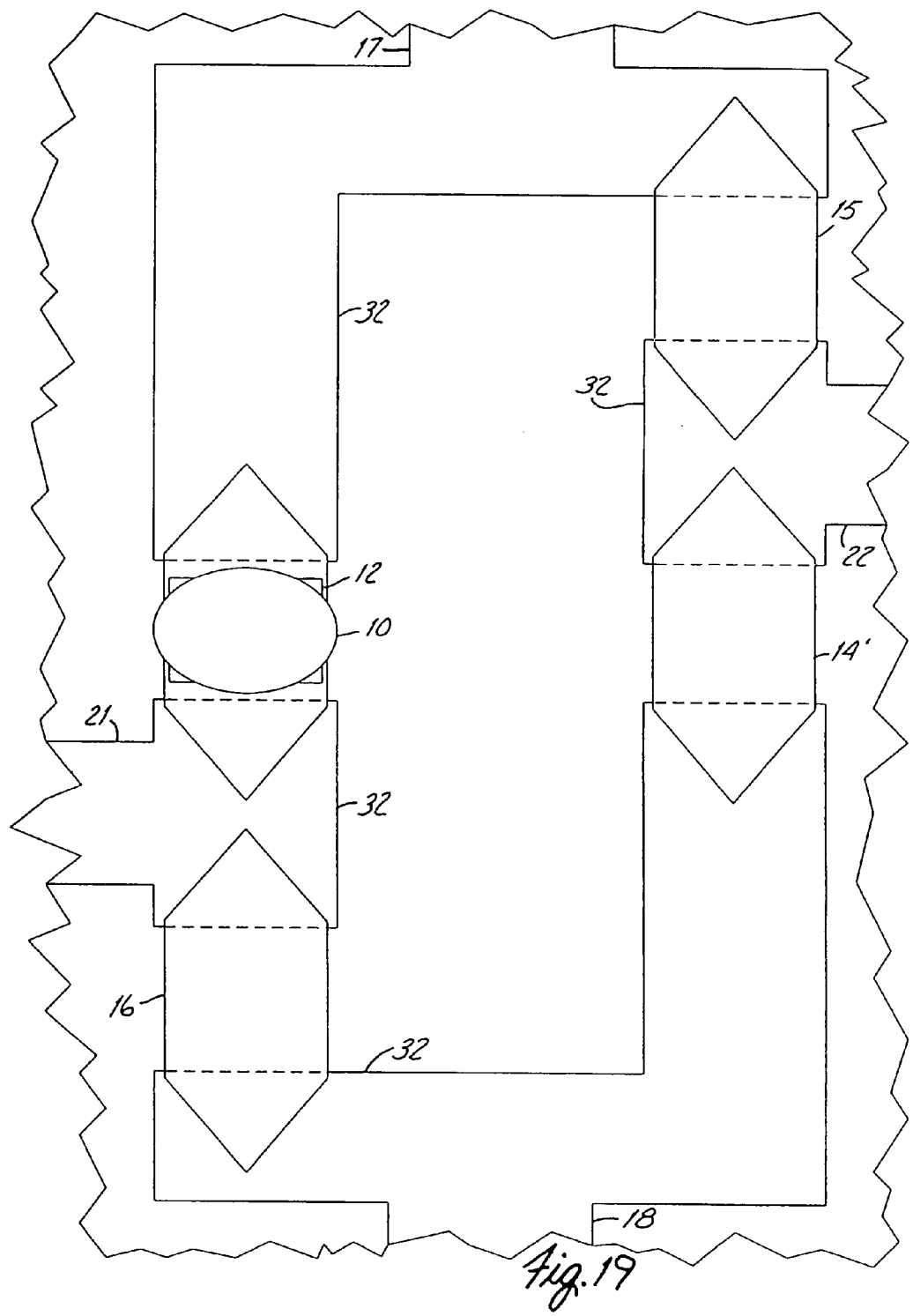

The FIG. 17 arrangement relying just on the binding molecule coating to keep a bead 10 in place is ideal if patterning the binding molecule coating is performed to provide portions thereof just where the magnetizable beads are desired to be attached. This way, the beads will stick only where they impart the largest field to the magnetoresistors. The form of the pattern depends on what sensing mode is being used. If the externally applied excitation magnetic field orientation is perpendicular to major surfaces of the magnetoresistors, the beads should come to be positioned next to or on top of the magnetoresistors as shown in the top views of FIGS. 18 and 19 which alternatively show the magnetoresistors interconnections above and below the magnetoresistors, respectively, in the shown detector portions. Since only one magnetoresistor 13 is actively affected by bead 10 here, the other magnetoresistor in the bridge circuit previously described as also being active in other arrangements has been redesignated 14' here. If the excitation orientation is parallel, the beads should come to be positioned on the magnetoresistors or between two magnetoresistors as in FIGS. 15, 16 and 17. Of course, the binding molecule coating material to which the beads come to stick in a position must be thin with respect to the thickness of detection devices layers (<1 μm). If the coating is instead tens of microns thick, then any magnetoresistor arrangement will be relatively insensitive.

Figure 20:
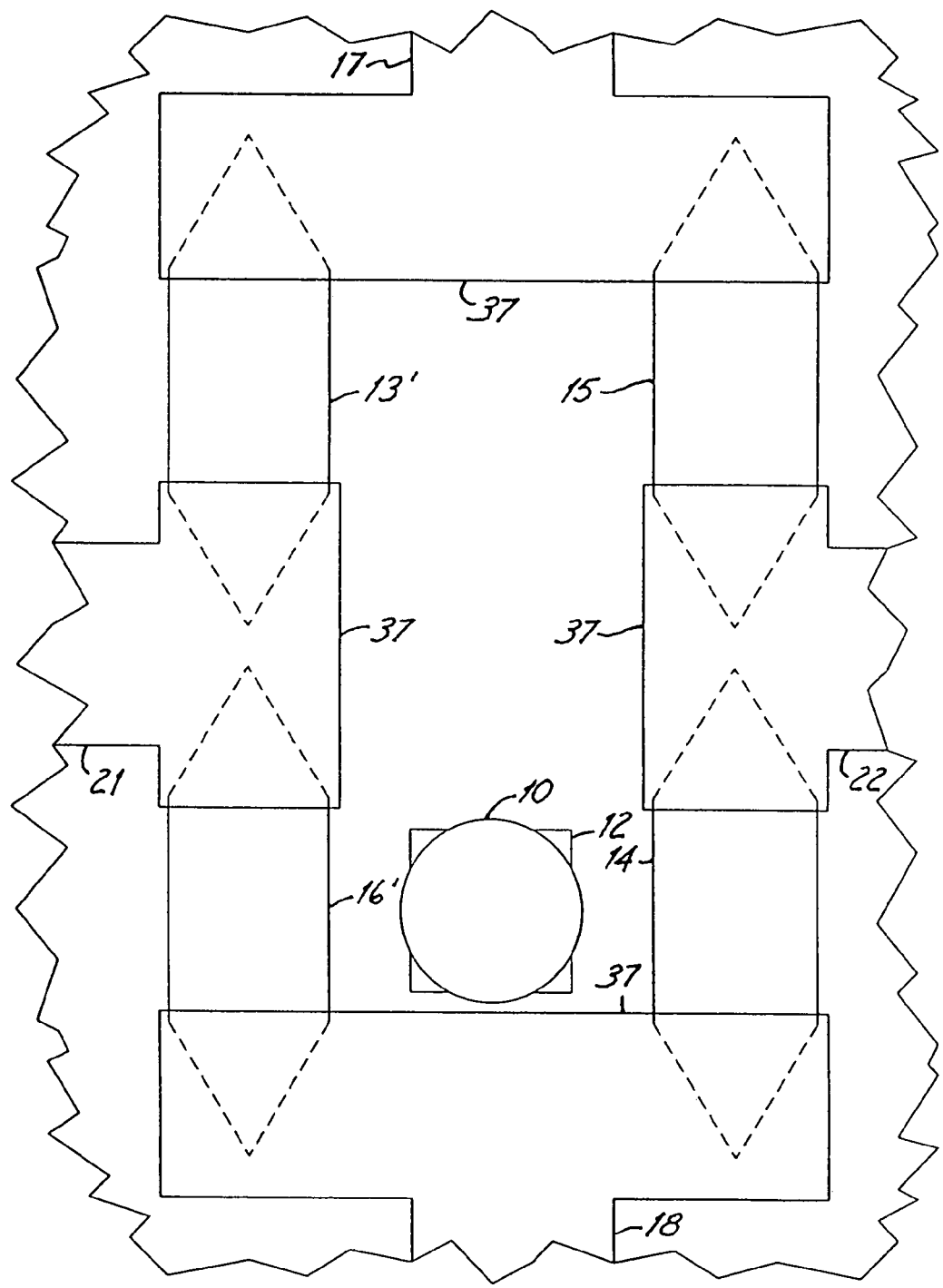

The magnetic field anomaly arising from the presence of a micron sized magnetizable bead is, in actuality, often very nonuniform and can be best detected in a differential mode using a gradiometer magnetic field measurement arrangement. In most situations, this means a bridge circuit configuration where one or two magnetoresistors of a four magnetoresistor bridge circuit experience the effects of the presence of a bead while the other two are not. That is, the "active" magnetoresistors are under the influence of the presence of a bead (since magnetoresistor 16 rather than magnetoresistor 13 is actively affected by bead 10 here along with magnetoresistor 14, this magnetoresistor in the bridge circuit previously described as being inactive in other arrangements has been redesignated 16' here) and the "reference" magnetoresistors are not so influenced as in FIG. 20.

If embedded externally applied magnetic field excitation coil straps and thick permeable masses as flux "pipes" are used on-chip to generate such externally applied magnetic fields locally around magnetoresistors, the presence of beads near the straps or resistors will change the local field distribution. Such bead presence will also change the field distribution in the gap between two flux concentrators. If a magnetoresistor is in the gap between two flux concentrators, the magnetic field experienced by them in the gap for the occurrence of an externally applied field will be reduced by the presence of a bead in the gap because they concentrate flux therethrough from the gap region and the magnetoresistors. A bridge sensor can be made to use this property by putting two magnetoresistors in a gap between flux concentrators where beads are allowed, or even promoted, to stick while putting two identical magnetoresistors in an otherwise identical gap between flux concentrators where beads are not allowed or promoted to stick. The externally applied magnetic field could be generated by on-chip current conductors located about the flux concentrators as in FIG. 10.

Figure 21:
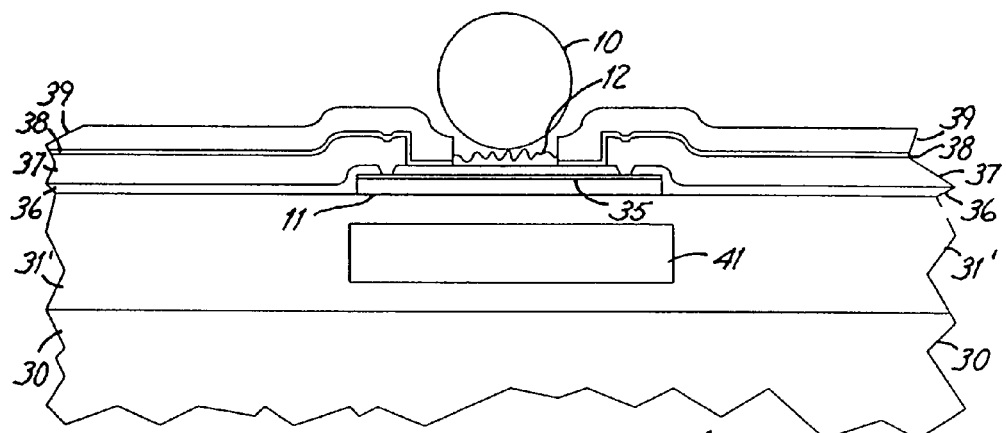
FIGS. 21 and 22 show layer diagrams of detector device portions embodying the present invention.
Figure 22:
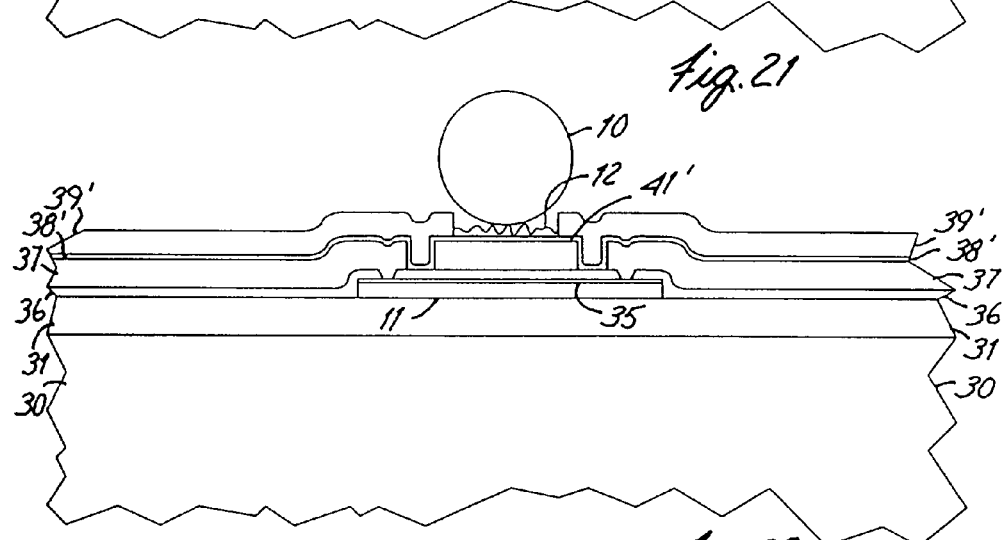

Beads near current conductors will redistribute magnetic flux generated by the current as well. If the beads are on the same side of the conductors as a magnetoresistor as in FIG. 21, the current generated magnetic field at the magnetoresistor due to current in such a conductor, 41, will be reduced. If the beads are on the opposite side of the conductor from the magnetoresistor, such as a conductor, 41', shown in FIG. 22, the current generated magnetic field will be increased. In the former situation, the beads form a higher magnetic permeability path and concentrate flux away from the magnetoresistor. In the latter case, the lower permeability of the beads permits a larger amount of flux to go around the conductor for a given amount of current therethrough.

Figure 23A:
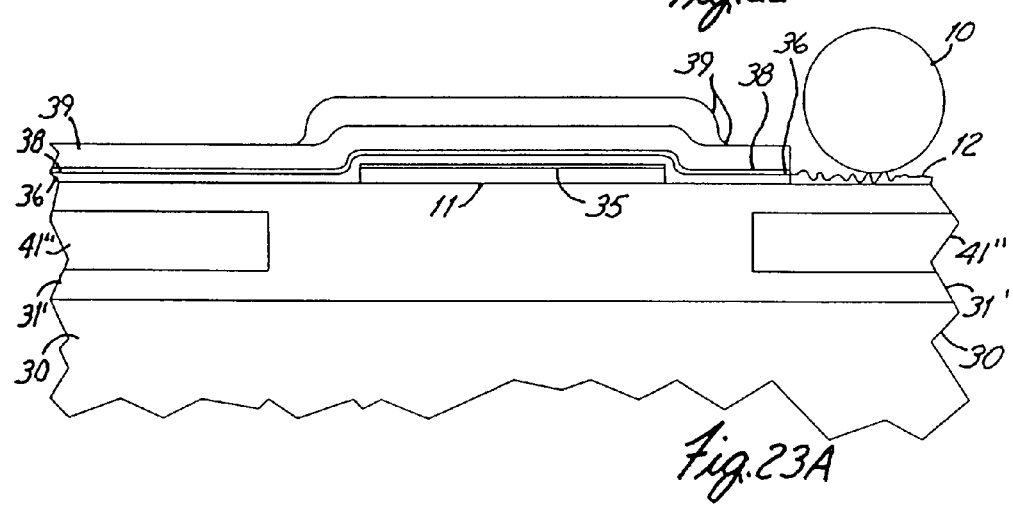
FIG. 23A shows a layer diagram of a detector device portion and FIG. 23B shows a top view of that device portion both embodying the present invention.
Figure 23B:
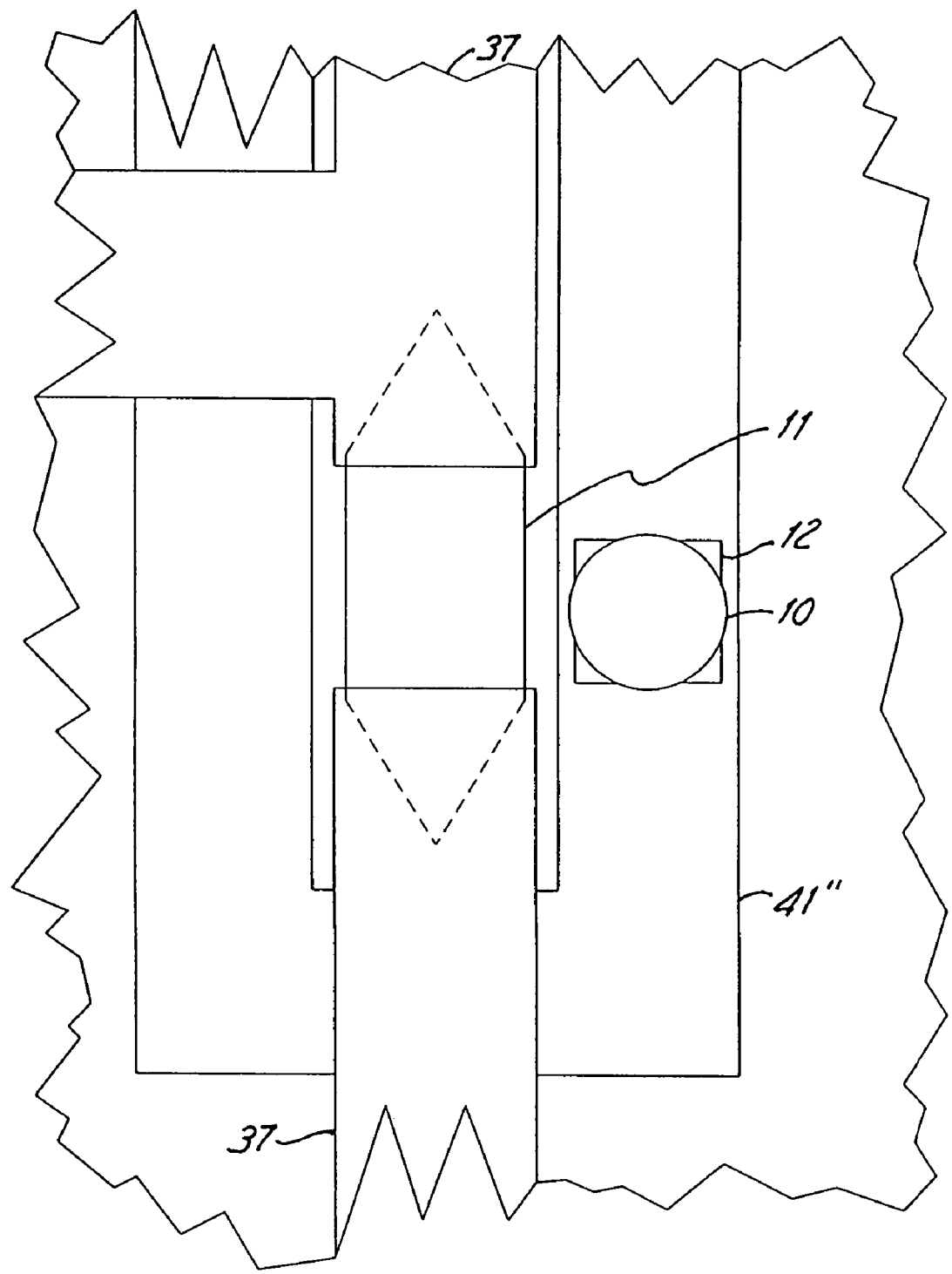

If a magnetoresistor is fabricated with the sensitive axis perpendicular to its direction of longest extent, with a buried, parallel current conductor provided around it at a fixed separation, the field along the sensitive axis would be zero at the magnetoresistor. If a bead came to be positioned above the conductor on one side of the magnetoresistor, such as a conductor, 41", shown in FIGS. 23A and 23B, the field would become unbalanced at the GMR resistor and a net field would be experienced to provide the basis for a four-magnetoresistor bridge circuit to generate an offset dependent output signal.

Figure 24:
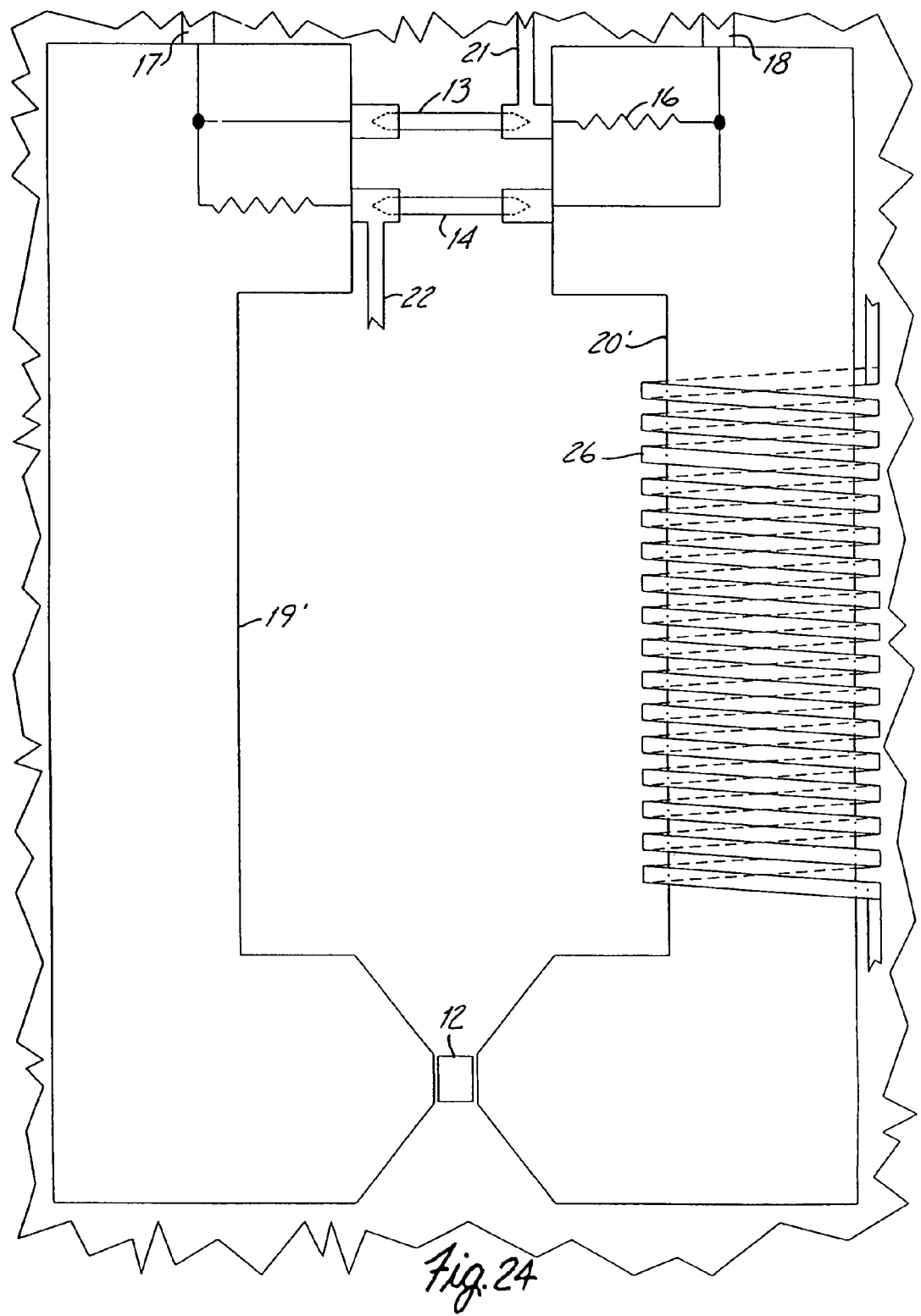
FIG. 24 shows a detector device portion embodying the present invention.

Typical magnetizable beads for assays require magnetic fields of several hundred to over a thousand Oe for saturation. Consequently, there is a mismatch between the field ranges of GMR magnetic field detector structure magnetoresistors and the fields required to significantly magnetize the beads. Because the saturation field for the beads is so large compared to the magnetoresistors, an arrangement to provide different flux densities for an externally applied excitation magnetic field would help. This can be done by making a permeable mass based flux loop on the detector surface with two types of gaps therein as shown in the detector arrangement portion shown in FIG. 24 with the permeable masses designated 19' and 20'. One gap is for beads in binding molecule coating region 12, and the other gap is for the active magnetoresistors. The reference magnetoresistors are positioned under the flux loop mass (shown schematically), or under other permeable mass shields. Both gaps have the same length along sensitive axes of the magnetoresistors (though this is not necessary). The gap for beads would be much narrower than the gap for the magnetoresistors. So while the same flux would pass across both gaps, the flux density would be much lower at the active magnetoresistor gap than at the bead gap. The flux loop permeable mass would ideally have coil 26 wound there around for current to generate the externally applied field. Alternatively, that field could be generated by an underlying planar coil.

Sample solution to be applied in assays using the magnetic detectors in integrated circuits of the kinds described above, containing various kinds of molecules possibly including the molecules selected for detection by the sensor along with label molecules attached to label beads (or particles) also present in the sample solution or in a supplemental solution concurrently also applied, must be controlled during such applications and properly directed to these detectors. This can be accomplished by providing enclosed receiving reservoirs ahead of the general magnetic detector locations and enclosed accumulation reservoirs thereafter, as well as one or more enclosed testing flow passageways or pools at the general magnetic detector locations, and enclosed channels between them as conduits for permitting the sample solutions under selected pressures to reach such reservoirs, passageways and pools without risk of contamination from outside sources thereof.

Figure 25:
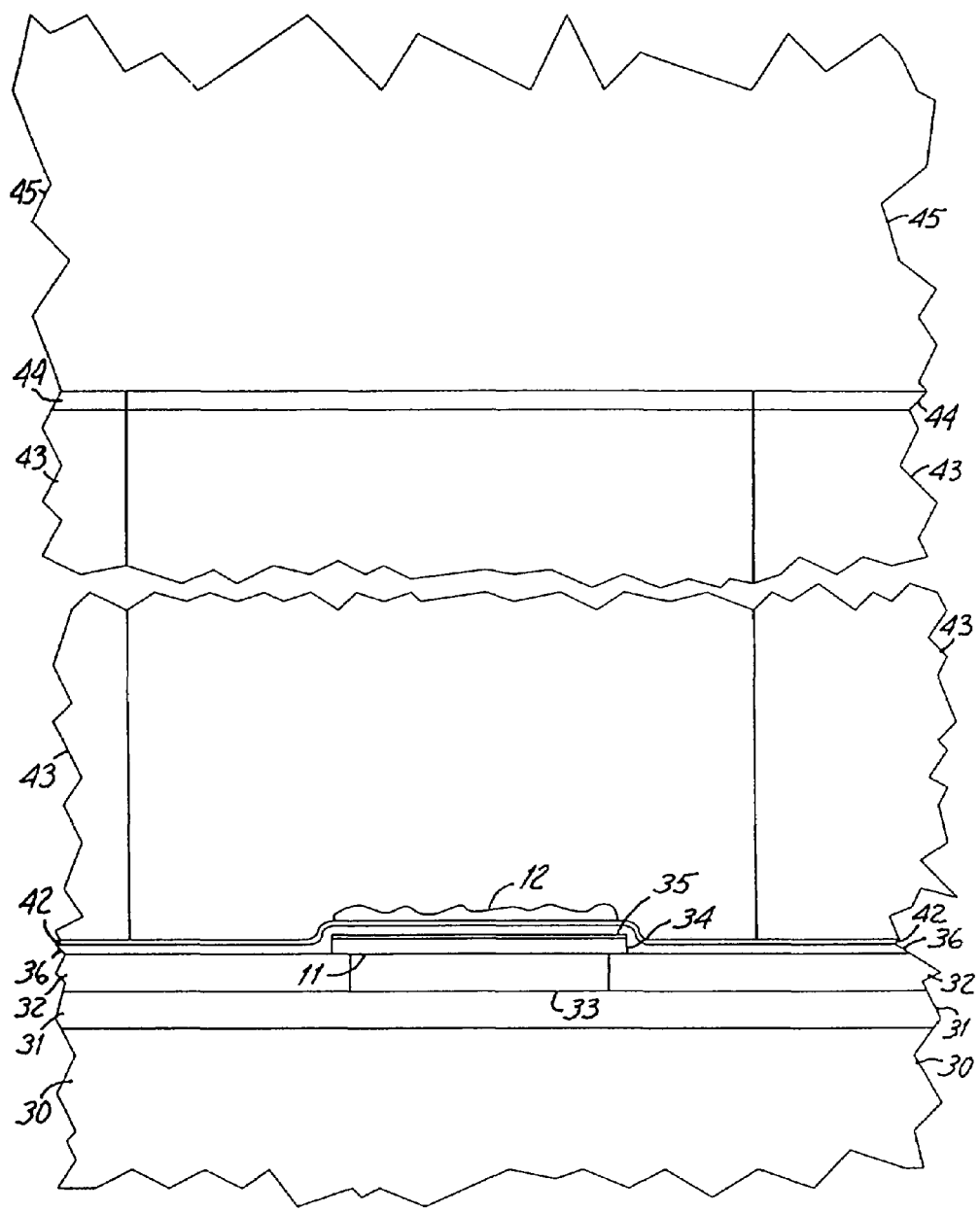
FIGS. 25, 26 and 27 show layer diagrams of detector device portions embodying the present invention.
Figure 26:
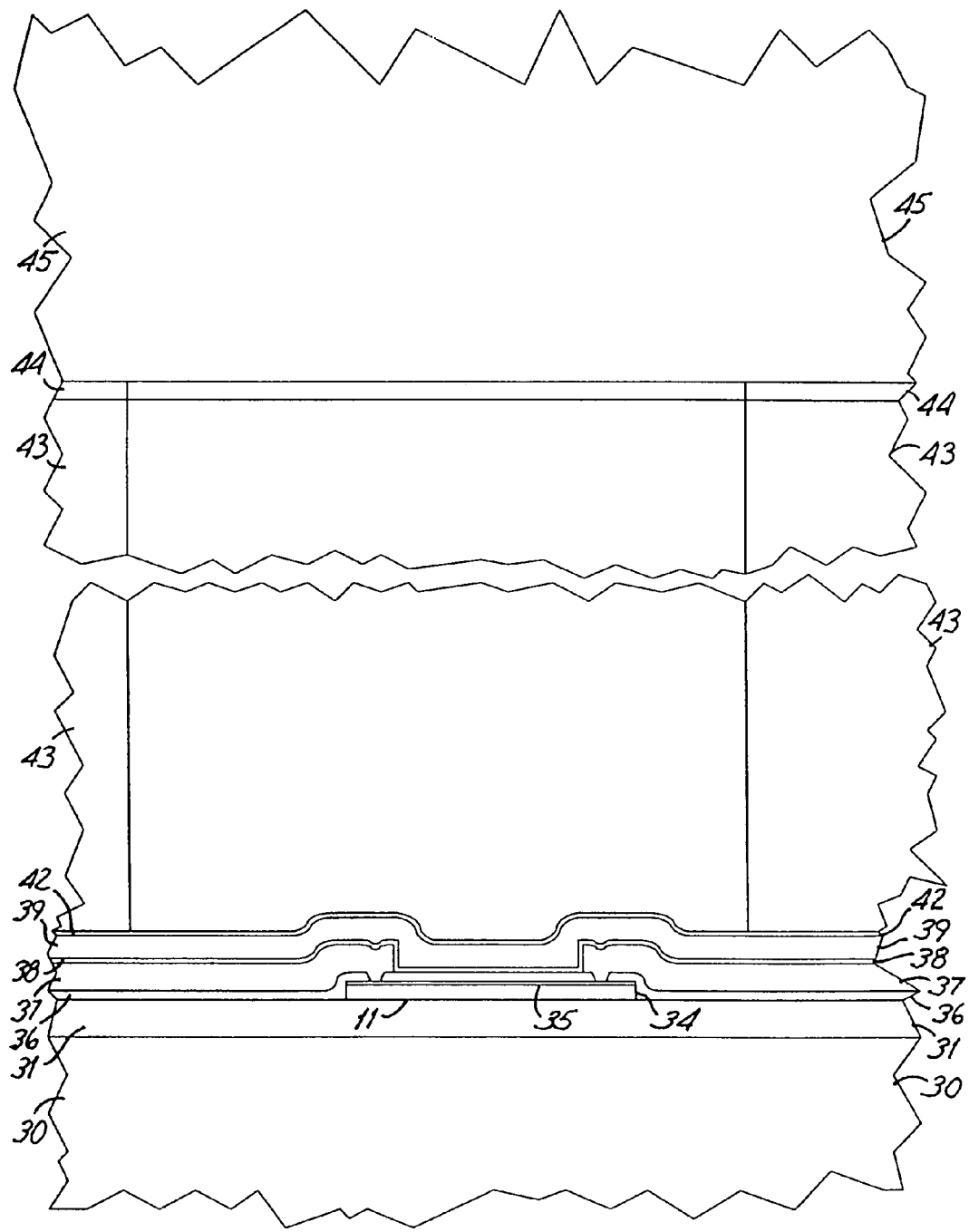
Figure 27:
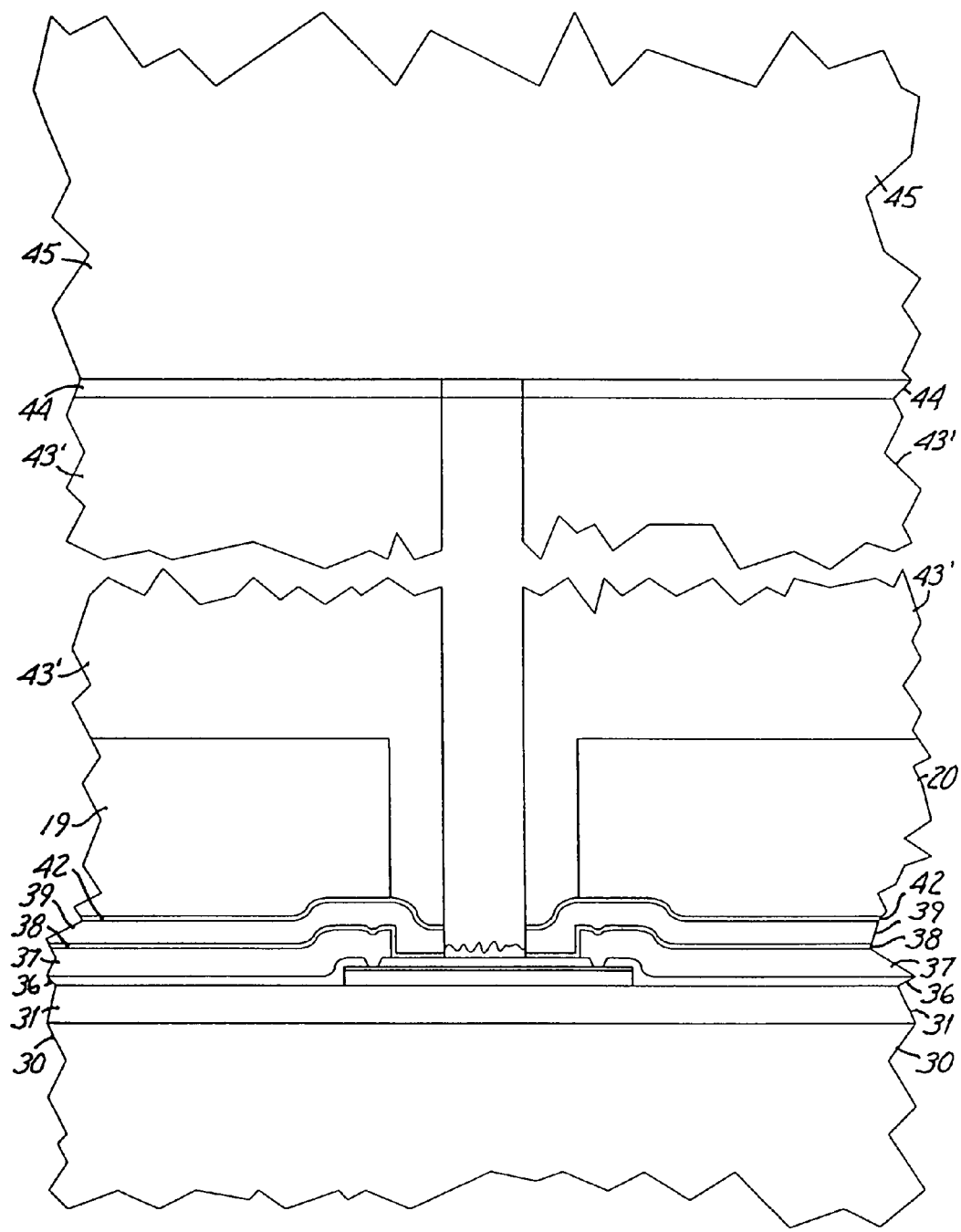

FIGS. 25, 26 and 27 show side views in layer diagrams of some of the magnetic detectors described above provided below passageways, pools or channels through which assay sample solutions can be provided to reach the vicinity of these detectors. FIG. 25 shows such an arrangement for the magnetic detector shown in FIG. 11, FIG. 26 shows such an arrangement for the magnetic detector shown in FIG. 8, and FIG. 27 shows such an arrangement for the magnetic detector shown in FIG. 9. Again, as in FIG. 9 versus FIG. 8, FIG. 27 is like FIG. 26 except that a $Si_3N_4$ portion of the outer passivation layer is removed from selected areas or some portion of that layer thereover is removed with molecular binding layer 12 afterward added there, and flux concentrators 19 and 20 are added for amplifying externally applied fields, or a coil and flux concentrator can be added for guiding on-chip developed magnetic fields.

In each of FIGS. 25, 26 and 27 an aluminum nitride (AlN) etch stop, 42, is first provided over the exposed surfaces shown in the corresponding previous detector drawings (FIGS. 11, 8 and 9) to a thickness of 300 Å by sputter deposition. Thereafter, a 5 µm positive photoresist layer is coated over etch stop 42 except in FIG. 27 where a much thicker layer is added to cover flux concentrators 19 and 20 perhaps as much as 20 µm depending on the thickness chosen for the flux concentrators. The photoresist is given a hard cure by heating through either a convection flow or on a hot plate sufficiently to cause the patterned resist to reach a temperature in excess of 200° C. Thereafter, a $Si_3N_4$ layer is sputter deposited on the photoresist to a thickness of 2000 Å. Standard photoresist methods are used to provide a masking pattern on this silicon nitride layer leaving openings where this layer and the BCB therebelow is to be removed by etching which is accomplished by reactive ion etching (RIE). A cured, patterned photoresist layer, 43, (43' in FIG. 27) results which serves as a dielectric, or electrical insulating material, base on the magnetic detector chip surface for a lid to be provided thereon to complete enclosing the desired reservoirs, passageways, pools and channels. In addition, a silicon nitride bonding material layer, 44, results thereon as a basis for attaching such a lid.

The polymer material chosen for layer 43 or 43' must be chosen with some care. The temperature at which it can be hard cured, or cross-linked, must be low enough to avoid damaging the magnetic detectors. The resulting material in the layer should exhibit low water absorption, and should further exhibit sufficient mechanical stiffness to support a lid and its attachment and to withstand the needed fluid pressures. The glass transition temperature of the material in layers 43 or 43' must be sufficiently high to exceed temperatures reached during thermosonic bonding. One suitable photoresist for use in forming dielectric polymer layers 43 or 43' is B-staged bisbenzocyclobutene (BCB) available from Dow Chemical Company in Midland, Mich. under the trade name CYCLOTENE in both photodefinable and nonphotodefinable versions.

In order to seal the desired reservoirs, passageways, pools and channels, polydimethy siloxane (PDMS; Sylgard 184, Dow corning, MI) was found suitable as a lid material due to its ability to be covalently attached to a number of substrates, its aptitude for conformal adhesion to a nonplanar substrate, and the ease of incorporating fluid interconnects within the polymer. In its native state cross-linked PDMS is hydrophobic with an idealized surface terminated by methyl groups. Exposure to an oxygen plasma affords a hydrophilic surface dominated by hydroxyl groups. When brought into contact with a silanol terminated surface (e.g., glass) an irreversible bond is formed. The mechanism of this linkage is believed to occur through a condensation reaction between the SiOH groups of the oxygen plasma treated PDMS and those of the substrate (Duffy). $Si_3N_4$ was chosen for the bonding layer 44 because its surface possesses $SiO_2$ and SiOH groups and it is easily deposited at micron dimensions on BCB.

A lid, 45, is constructed by curing PDMS at 70° C. on a positive mold that resulted in nanoliter chambers on the bonding surface of the cover. When the cover is aligned properly with layer 44, these chambers coincide with the desired reservoirs. Layer 44 provided a surface that formed an irreversible bond with the PDMS in lid 45 after oxygen plasma treatment.

The oxygen plasma treatment of the PDMS and the $Si_3N_4$ is performed in a series of steps. First, the integrated circuit chip with the magnetic detectors and layer 44 is rinsed with isopropanol and dried under flowing $N_2$. The chip is then treated for two minutes at an oxygen pressure of 800 mtorr and a forward power of 300 W in an RF generated plasma. Both the PDMS and chip are then placed in the oxygen plasma for twelve seconds, removed and placed in contact with each other. The chip assembly is then heated to 70° C. for ten minutes.

Figure 14:
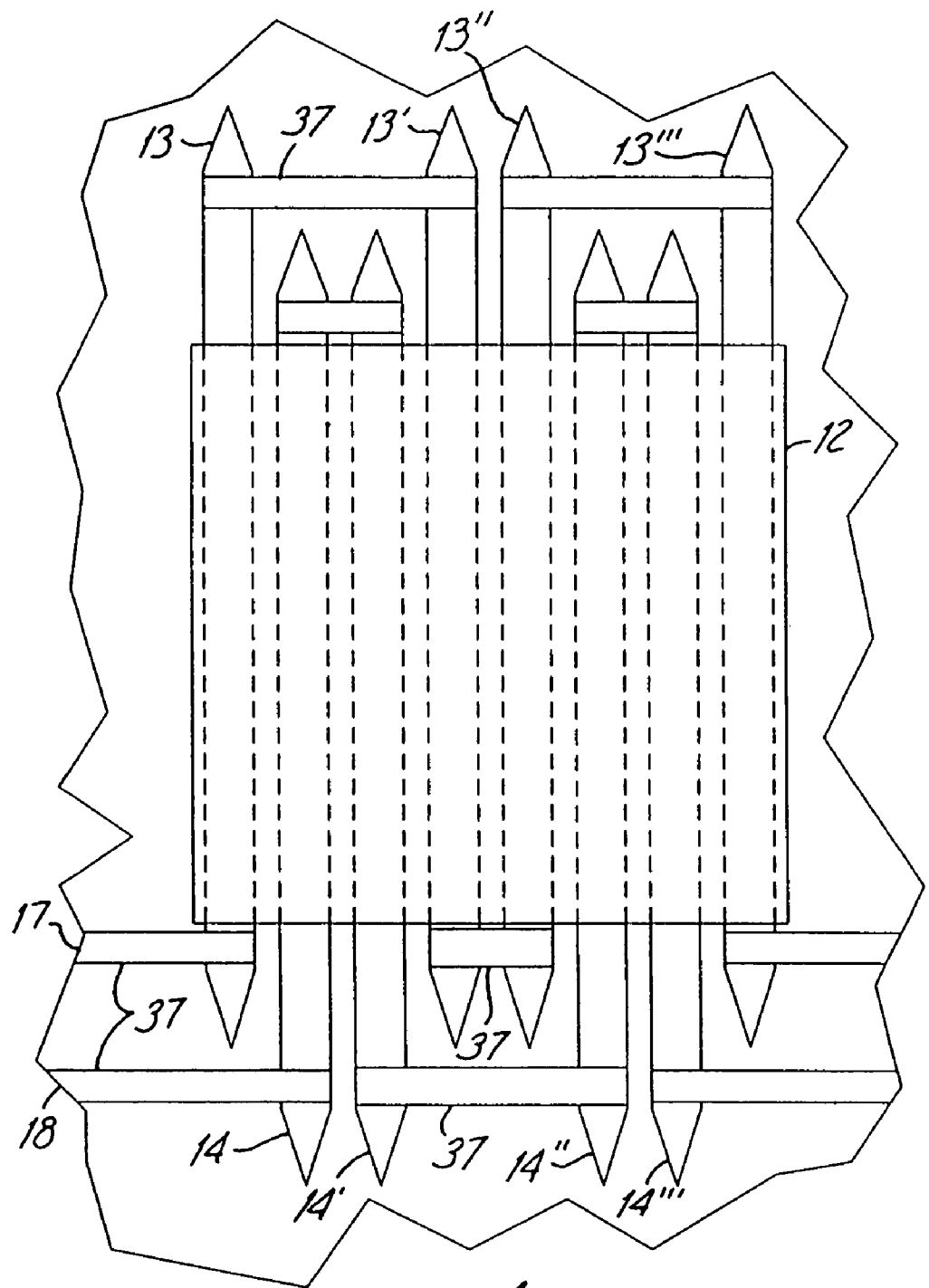
Figure 28:
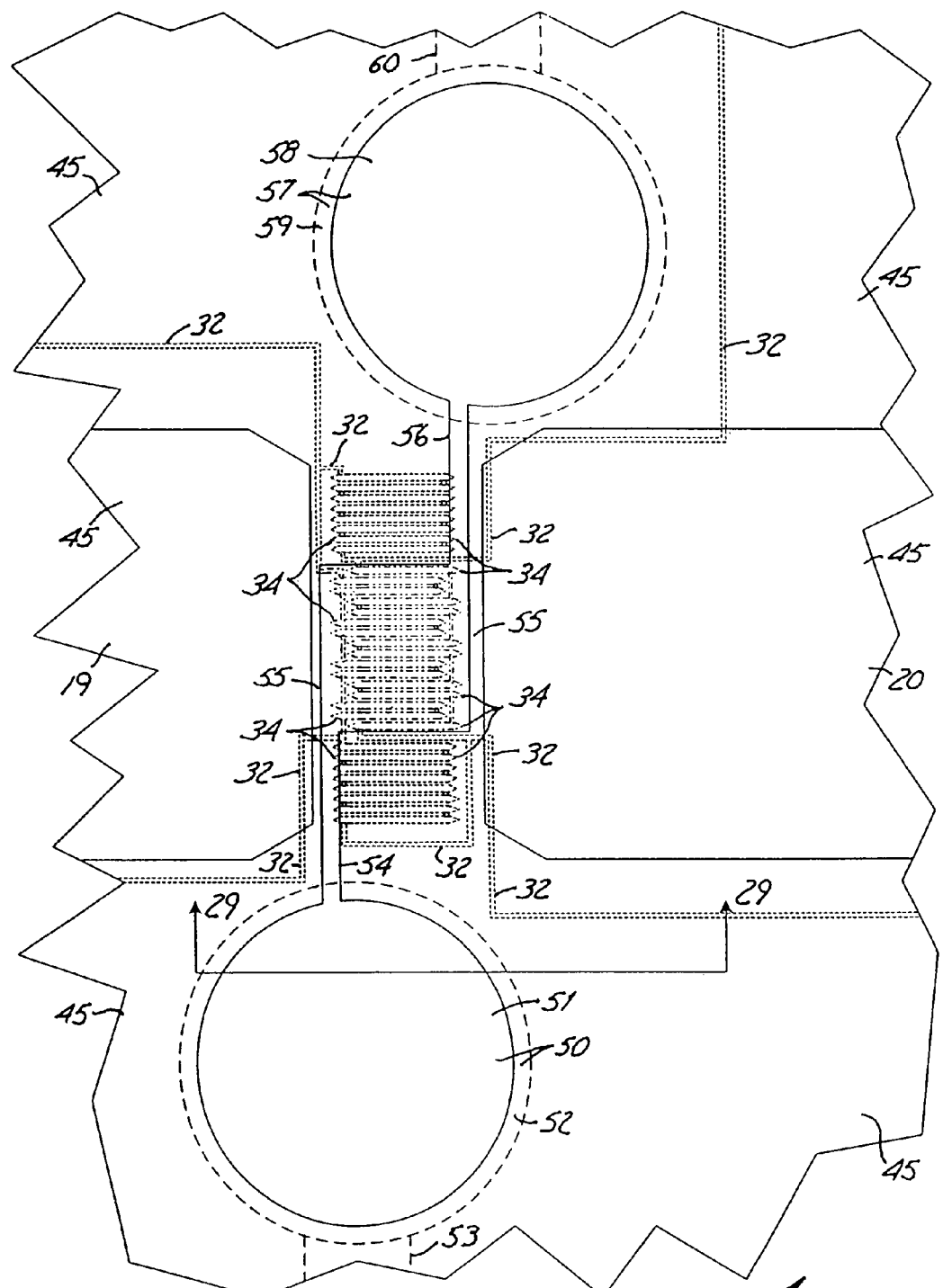
FIG. 28 shows a detector device portion embodying the present invention.

A top view of a portion of a more complete monolithic integrated circuit chip magnetic detector based assay sample solution analysis system is shown in FIG. 28 based on the interleaved magnetic field detector magnetoresistors of FIG. 14 but with the under-the-magnetoresister interconnection arrangement of FIGS. 11 and 25 rather than the over-the-resistor interconnection arrangement of FIGS. 8, 9, 26 and 27 actually shown in FIG. 14. Lid 45 is shown in place with an inlet reservoir, 50, provided by an inlet pool, 51, formed in the BCB base and in the integrated circuit chip, and an inlet chamber, 52, molded into lid 45. An inlet capillary, 53, is inserted from the side of PDMS material lid 45 therethrough into inlet chamber 52 that can be connected to a syringe to supply the sample solution for analysis. Inlet capillary 53 is a polyimide coated fused silica capillaries (350 μm OD, 250 μm ID; Polymicro Technologies, AZ).

Constant pressure applied to a connected syringe containing the sample solution will induce fluid flow through the capillary to inlet reservoir 50 from where, after the filling of that reservoir, the fluid will flow through an inlet channel, 54, to an analysis pool, 55, over magnetoresistors 34 of the magnetic field detector bridge circuit. After the detection of any magnetic fields associated with the sample solution, the solution travels on to an outlet channel, 56, to an outlet reservoir, 57, provided by an outlet pool, 58, formed in the BCB base and in the integrated circuit chip, and an outlet chamber, 59, molded into lid 45. An outlet capillary, 60, is inserted from the side of PDMS material lid 45 therethrough into outlet chamber 59 from which the sample solution can exit. Inlet pool 51, inlet channel 54, analysis pool 55, outlet channel 56 and outlet pool 58 are shown in solid lines for clarity, as are flux concentrators 19 and 20, even though they are all positioned below the top of lid 45.

Figure 29:
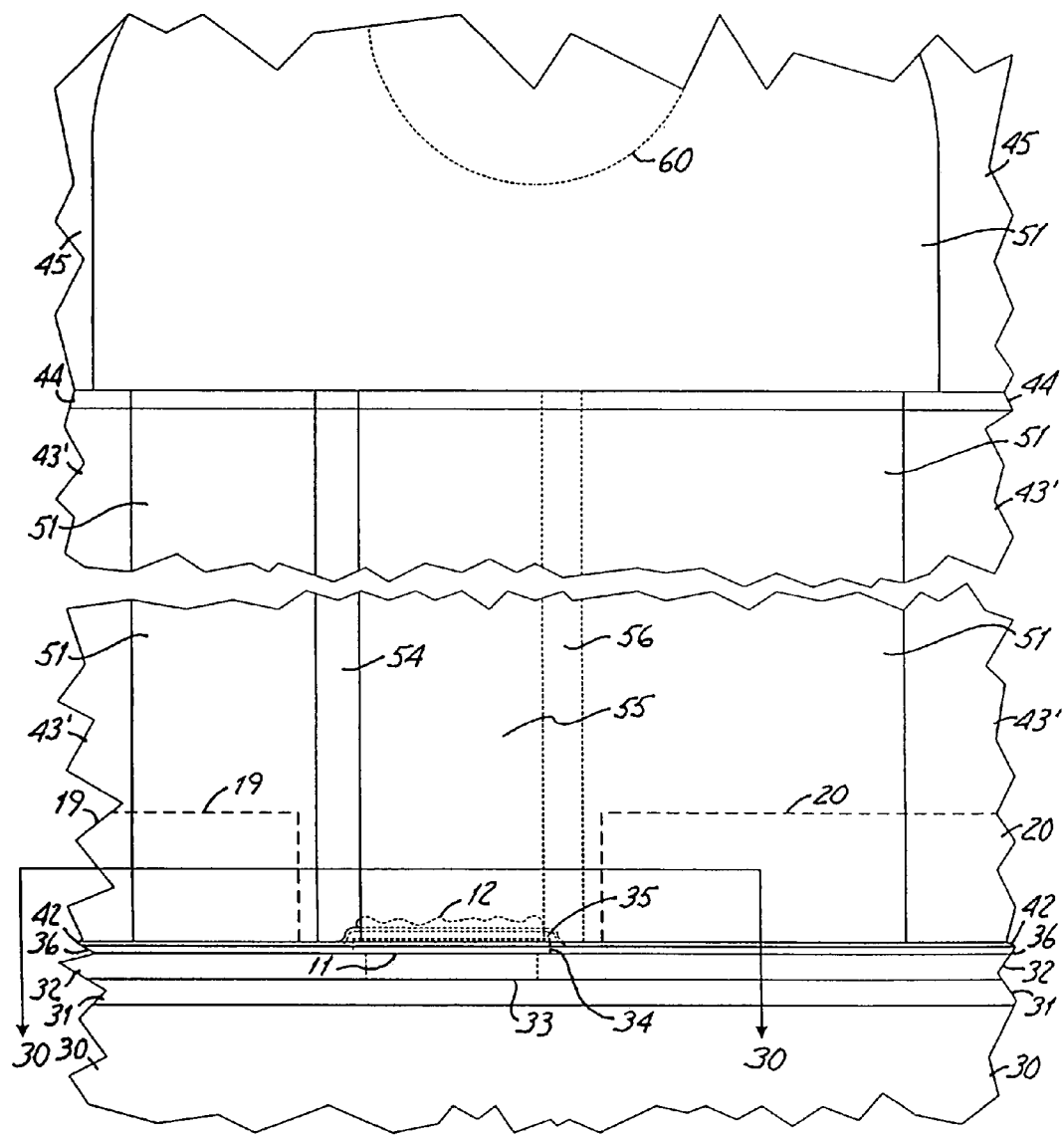
FIG. 29 shows a layer diagram of the detector device portion of FIG. 28.
Figure 30:
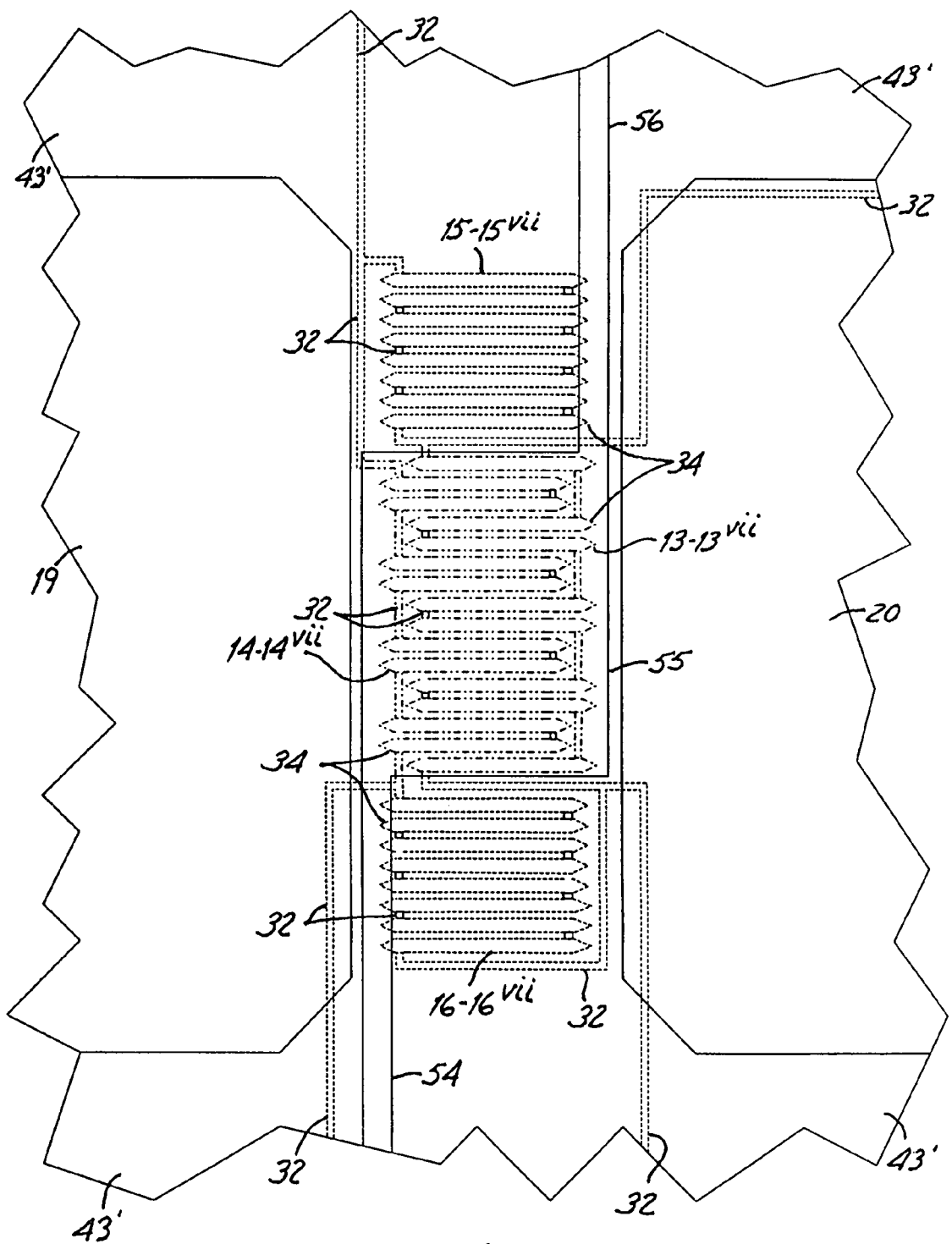
FIG. 30 shows a part of the detector device portion of FIGS. 28 and 29.

A side section view in a layer diagram of a portion of what is shown in FIG. 28 as marked there is shown in FIG. 29. This view is taken from inlet reservoir 50 looking toward outlet reservoir 57 through inlet channel 54 and analysis pool 55. A closer look at analysis pool 55 is given in a top view thereof in FIG. 30 as marked in FIG. 29.

In operating a bridge circuit with the magnetic field detectors based on magnetoresistors as described above, the absence of any magnetized beads over a magnetoresistor results in that magnetoresistor operating on its basic resistance (R) or magnetoresistor output voltage (v, acquired from the resistance change by passing a sense current therethrough) versus the externally applied magnetic field $(H_a)$ characteristic such as that shown by the solid line characteristic in FIG. 31. The resistance is relatively high near to zero fields where the magnetizations of the two ferromagnetic layers in such a magnetoresistor are directed away from one another, and decreases in the presence of larger magnitude applied magnetic fields as the magnetizations of each layer are forced toward a common direction thereby.

The addition of magnetized beads very close to such a magnetoresistor does not alter the general shape of the resistance versus applied magnetic field characteristic thereof but effectively spreads it wider over the applied magnetic field axis as those beads act to shunt part of the applied magnetic field away from that magnetoresistor. The result is shown as the dashed line resistance or magnetoresistor output voltage versus the externally applied magnetic field characteristic in FIG. 31. The shunting effect shown here is about 10% of the total field, i.e. it takes 10% more field to saturate the GMR resistor completely covered with beads than to saturate one with no beads. Fewer beads near the magnetoresistor results in a smaller effect.

A bridge circuit magnetic field detection arrangement such as that shown in FIG. 7 can be used to make accurate measurements of the surface bead concentration near sensing magnetoresistors by having two opposite bridge magnetoresistor exposed to the possibility of magnetized bead coverage and the other two not so exposed. Again a constant voltage source is used to supply electrical power to the bridge circuit and a high impedance amplifier is used to provide the bridge output signal a voltage measuring device as a basis for monitoring the bridge output signal. The bridge circuit magnetoresistors are assumed to be well matched to one another so that the characteristics of those magnetoresistors in the absence of magnetized beads are all like that of the solid line characteristic in FIG. 31, and like that of the dashed line characteristic in FIG. 31 for both of the pair of magnetoresistors that can be exposed to magnetized beads.

If the pair of bridge circuit resistors exposed to having magnetized beads nearby have the maximum number of such beads in the effective sensing vicinity thereof present, seemingly a good reference measurement of the bridge output can be made at zero externally applied magnetic field because the resistances of all resistors will be nominally equal (i.e., when the beads are not magnetized so that they are not shunting away any of the magnetizing field from the magnetoresistors) for well matched magnetoresistors. Thereafter, single polarity or bipolar externally applied magnetic field value excursions about the zero field value can be applied, as indicated by the horizontal double headed arrow crossing the zero applied field value in FIG. 31, to measure bridge circuit output signal voltages from this reference to determine the number of beads present near the sensing pair of magnetoresistors. However, the resistances of magnetoresistors at zero applied magnetic field actually drift with time due to the considerable magnetic hysteresis in the GMR material used in their construction as is indicated by the dashed lines in the characteristics shown in FIG. 31 near zero externally applied magnetic fields. This hysteresis leads to random magnetization orientation changes that appear as output signal noise and drift in the measurement.

A more stable null measurement can be made at larger externally applied magnetic fields. Above the externally applied magnetic field value $H_{saturate}$ in FIG. 31, both pairs of bridge magnetoresistors are magnetically saturated and so again have equal resistance values for well matched magnetoresistors. Thus, the bridge circuit magnetoresistor resistances at $H_{saturate}$ are balanced and the bridge output signal value is zero. At a lower externally applied magnetic field value of $H_{sense}$ below $H_{saturate}$, the resistances of the two pairs of bridge magnetoresistors are unequal due to the shunting effect of the magnetized beads being in the effective sensing vicinity of one of those pairs. Thus, the bridge circuit magnetoresistor resistances at $H_{sense}$ are now unbalanced and the bridge output signal becomes nonzero.

Hence, the number of magnetized beads present near the pair of magnetoresistors exposed thereto can be measured by providing an externally applied field that changes from $H_{saturate}$ to $H_{sense}$ as indicated by the horizontal double headed arrow therebetween in FIG. 31. The effective output signals of the measurement system, then, are the differences between bridge circuit voltage outputs that occur at the externally applied field value $H_{saturate}$ (zero since there is no difference the characteristics of the two pairs at that applied field value) and those that occur at the applied field value $H_{sense}$ (which is based on the difference between the solid line and dashed line characteristics at that applied field value) as indicated by the vertical double headed arrow showing the difference between the solid and dashed line characteristics at that applied field value.

This differential measurement technique (based on two different externally applied fields) also permits canceling of low frequency (1/f) noise otherwise resulting in individual measurements. A preferred arrangement would be to oscillate the externally applied field between $H_{sense}$ and $H_{saturate}$ at a frequency above the corner frequency of the 1/f noise (say 25 kHz) to thereby be operating where this noise is a minimum, and then measure the peak-to-peak value of the output. Typical values for $H_{sense}$ and $H_{saturate}$ would be 300 Oe and 400 Oe, respectively, for multilayer material. Other GMR materials that saturate more easily would have $H_{sense}$ and $H_{saturate}$ of 60 and 80 Oe. There are several possible types of GMR material, each with good and bad features. Those requiring high fields to saturate have good linearity and low hysteresis. Those requiring lower fields to saturate have more hysteresis and may require too much current density for the heat budget of the measurement. Regardless of which GMR material is used, the key requirement is to make a reference measurement above the saturation field of the resistors exposed to beads and a sense measurement at a field where both pairs are not saturated.

In a practical miniaturized system, it is not practical to generate 300-400 Oe fields over any volume due to the electrical power requirements for doing so. One way to increase the effective field at the measurement bridge is to use flux concentrators to "amplify" the field. A typical amplification factor would be 15×. In this case, only 20 to 27 Oe would be required. This is much easier to accomplish in terms of the needed electrical power. Oscillating the externally applied field between $H_{sense}$ and $H_{saturate}$ at a selected frequency can be accomplished in an arrangement like that shown in FIG. 10.

Although the present invention has been described with reference to preferred embodiments, workers skilled in the art will recognize that changes may be made in form and detail without departing from the spirit and scope of the invention.

The invention claimed is:

1. A method for detecting magnetic particles contained in a fluid provided in an extended gap opening formed in a channel base material supported on at least a portion of a substrate where a magnetic field sensor is also supported on at least a portion of said substrate but without said channel base material being across said magnetic field sensor from said substrate so as to form sides of said extended gap opening there that extends past said magnetic field sensor in at least one direction, there being an electrical conductor supported on said substrate positioned at least in part at said sensor location so as to be in direct contact with at least some surface of said magnetic field sensor positioned at least in part along, and between projections at said sides of, said extended gap opening, said method comprising:

introducing said fluid with said magnetic particles contained therein into said extended gap opening so as to be present at a vicinity about said magnetic field sensor;

supplying a selected first electrical current in said electrical conductor and said magnetic field sensor while monitoring that voltage occurring across said magnetic field sensor; and supplying a magnetic field from a source other than said magnetic particles in a selected direction such that said magnetic field is present in said extended gap opening.

2. The method of claim 1 wherein said selected direction of said magnetic field is from one said side of said extended opening forming said channel gap at least at said vicinity of said magnetic field sensor to an opposite side thereof to thereby extend through said extended gap opening substantially perpendicular to said sides there.

* * * * *